US008791158B2

(12) United States Patent
Dalton et al.

(10) Patent No.: US 8,791,158 B2
(45) Date of Patent: Jul. 29, 2014

(54) METHODS OF TREATING MEIBOMIAN GLAND DYSFUNCTION

(75) Inventors: James T. Dalton, Lakeland, TN (US); Jeetendra Eswaraka, Carlsbad, CA (US)

(73) Assignee: GTX, Inc., Memphis, TN (US)

(\*) Notice: Subject to any disclaimer, the term of this patent is extended or adjusted under 35 U.S.C. 154(b) by 174 days.

(21) Appl. No.: 13/004,764

(22) Filed: Jan. 11, 2011

(65) Prior Publication Data

US 2011/0172302 A1 Jul. 14, 2011

Related U.S. Application Data

(60) Provisional application No. 61/293,966, filed on Jan. 11, 2010.

(51) Int. Cl.
*A01N 37/34* (2006.01)
*A61K 31/275* (2006.01)

(52) U.S. Cl.
USPC .......................................... 514/522; 514/912

(58) Field of Classification Search
None
See application file for complete search history.

(56) References Cited

U.S. PATENT DOCUMENTS

| | | | |
|---|---|---|---|
| 4,407,791 A | 10/1983 | Stark | |
| 4,636,505 A | 1/1987 | Tucker | |
| 6,492,554 B2 | 12/2002 | Dalton et al. | |
| 6,777,427 B2 | 8/2004 | Miyakawa et al. | |
| 6,838,484 B2 | 1/2005 | Steiner et al. | |
| 6,998,500 B2 | 2/2006 | Dalton et al. | |
| 7,022,870 B2 | 4/2006 | Dalton et al. | |
| 7,026,500 B2 | 4/2006 | Dalton et al. | |
| 7,214,693 B2 | 5/2007 | Dalton et al. | |
| 7,595,402 B2 * | 9/2009 | Miller et al. | 546/158 |
| 7,622,503 B2 | 11/2009 | Dalton et al. | |
| 7,645,898 B2 | 1/2010 | Dalton et al. | |
| 7,705,182 B2 | 4/2010 | Chen et al. | |
| 7,772,433 B2 | 8/2010 | Dalton et al. | |
| 8,080,682 B2 | 12/2011 | Dalton et al. | |
| 2003/0225040 A1 | 12/2003 | Dalton et al. | |
| 2004/0029913 A1 | 2/2004 | Dalton et al. | |
| 2004/0087810 A1 | 5/2004 | Dalton et al. | |
| 2004/0147489 A1 | 7/2004 | Dalton et al. | |
| 2004/0197928 A1 | 10/2004 | Dalton et al. | |
| 2004/0224979 A1 | 11/2004 | Chen et al. | |
| 2004/0260092 A1 | 12/2004 | Chung et al. | |
| 2004/0260108 A1 | 12/2004 | Dalton et al. | |
| 2004/0265916 A1 | 12/2004 | Dalton et al. | |
| 2005/0033074 A1 | 2/2005 | Dalton et al. | |
| 2005/0038110 A1 | 2/2005 | Steiner et al. | |
| 2006/0009488 A1 * | 1/2006 | Miller et al. | 514/312 |
| 2006/0035965 A1 | 2/2006 | Dalton et al. | |
| 2006/0111441 A1 | 5/2006 | Dalton et al. | |
| 2006/0229362 A1 | 10/2006 | Dalton et al. | |
| 2006/0276539 A1 | 12/2006 | Dalton et al. | |
| 2007/0066568 A1 | 3/2007 | Dalton et al. | |
| 2007/0082017 A1 | 4/2007 | Tseng | |
| 2007/0123563 A1 | 5/2007 | Dalton et al. | |
| 2007/0161608 A1 | 7/2007 | Dalton et al. | |
| 2007/0173546 A1 | 7/2007 | Dalton et al. | |
| 2007/0281906 A1 | 12/2007 | Dalton et al. | |
| 2008/0076828 A1 | 3/2008 | Dalton et al. | |
| 2008/0312194 A1 | 12/2008 | Abelson et al. | |
| 2009/0088480 A1 | 4/2009 | Ahn et al. | |
| 2009/0156614 A1 | 6/2009 | Dalton et al. | |
| 2010/0022641 A1 | 1/2010 | Ahn et al. | |
| 2010/0137430 A1 | 6/2010 | Dalton et al. | |
| 2010/0249228 A1 | 9/2010 | Dalton et al. | |
| 2011/0237664 A1 | 9/2011 | Dalton et al. | |
| 2012/0136052 A1 | 5/2012 | Dalton et al. | |
| 2013/0034562 A1 | 2/2013 | Dalton et al. | |

FOREIGN PATENT DOCUMENTS

| | | |
|---|---|---|
| WO | WO03074449 A2 | 9/2003 |
| WO | WO03074471 A1 | 9/2003 |
| WO | WO03106401 A1 | 12/2003 |
| WO | WO2004034978 A2 | 4/2004 |
| WO | WO2004035736 A2 | 4/2004 |
| WO | WO2004035738 A2 | 4/2004 |
| WO | WO2004035739 A2 | 4/2004 |
| WO | WO2004035736 A3 | 7/2004 |
| WO | WO2004064747 A2 | 8/2004 |
| WO | WO2005060647 A2 | 7/2005 |
| WO | WO2005120483 A2 | 12/2005 |
| WO | WO 2007/027582 A2 | 3/2007 |
| WO | WO2007027582 A2 | 3/2007 |
| WO | WO2008008433 A2 | 1/2008 |
| WO | WO2008024456 A2 | 2/2008 |
| WO | WO2008127717 A1 | 10/2008 |
| WO | WO 2009/137602 A1 | 11/2009 |
| WO | WO2012139093 A2 | 10/2012 |

OTHER PUBLICATIONS

Sullivan et al, Annals New York Academy of Sciences, 2002, vol. 966, pp. 211-222.*
National Eye Institute (NEI) website—Dry Eye, content last reviewed in Aug. 2009.*
Sullivan et al, Investigative Ophthalmology and Visual Science, Nov. 2000, vol. 41, pp. 3732-3742.*
Hom Mm et al., "Prevalence of Meibomian Gland Dysfunction," Optometry and Vision Science, 67(9), 710-2, 1990.
Ong Bl, "Relation between Contact Lens Wear and Meibomian Gland Dysfunction," Optometry and Vision Science, 73(3), 208-10, 1996.
McCulley et al., "Meibomian gland and tear film lipids: structure, functiona nd control," Adv Exp Med Biol., 506 (Pt A), 373-8, 2002.
Sullivan et al., "Androgen deficiency, Meibomian gland dysfunction, and evaporative dry eye," Ann. NY Acad. Sci., 966, 211-222, 2002.
Sullivan et al., "Androgen Influence on the Meibomian Gland," IOVS, 41(12), 3732-3742, 2000.

(Continued)

*Primary Examiner* — Brian-Yong Kwon
*Assistant Examiner* — Mark V Stevens
(74) *Attorney, Agent, or Firm* — Pearl Cohen Zedek Latzer Baratz LLP; Mark S. Cohen

(57) ABSTRACT

The present invention includes methods for treating Meibomian gland dysfunctions. The invention also includes methods for improving tear lipid composition, for treating abnormal Meibomian gland secretion and for normalizing Meibomian gland secretions.

52 Claims, 4 Drawing Sheets

(56) References Cited

OTHER PUBLICATIONS

Ofri R., et al., "Canine meibometry: Establishing baseline values for meibomian gland secretions in dogs," The Veterinary Journal, 174, 536-540, 2007.

Joffre et al., "Differences in meibomian fatty acid composition in patients with meibomian gland dysfunction and aqueous-deficient dry eye" British Journal of Ophthalmology, vol. 92, Issue 1, 2008, abstract.

Foulks et al., "Blepharitis: A Review for Clinicians," Refractive Eyecare vol. 13, No. 3, 2009, p. 6 [http://www.refractiveeyecare.com/pdfs/re-blepharitis-web-1—s-20.pdf] .

International Search Report and Written Opinion of corresponding PCT Application No. PCT/US11/20871 dated Mar. 22, 2011.

Allan, "Induction of a novel conformation in the progesterone receptor by ZK299 involves a defined region of the carboxyl-terminal tail", Mol Endocrinol. Oct. 1996; 10(10):1206-13.

Bhasin S, Calof OM, Storer TW, Lee ML, Mazer NA, Jasuja R, Montori VM, Gao W, Dalton JT. Drug insight: Testosterone and selective androgen receptor modulators as anabolic therapies for chronic illness and aging. Nature, Clinical Practice in Endocrinology and Metabolism, 2(3): 146-159,2006.

Bisson WH, Cheltsov $AV_5$Bruey-Sedano N, Lin B, Chen J, Goldberger N, May LT, Christopoulos A, Dalton Jt, Sexton PM, Zhang XK, Abagyan R. Discovery of antiandrogen activity of nonsteroidal scaffolds of marketed drugs. Proceedings of the National Academy of Sciences, U S A. 104(29): 1192741932, 2007.

Bohl CE, Chang C, Mohler M, Miller DD, Swaan PW, and Dalton JT. A Ligand-based Approach to Identify Quantitative Structure Activity Relationships for the Androgen Receptor. The AAPS Journal, vol. 6, No. 4, Abstract #W4111, Nov. 2004.

Bohl CE, Wu Z, Miller DD, Bell CE, Dalton JT. Crystal structure of the TS77A human androgen receptor Ugand-binding domain completed to cyproterone acetate provides insight for ligand-induced conformational changes and structure-based drug design. Journal of Biological Chemistry, 282(18):13648-13655,2007.

Buchwald et al. "Long-term, continuous intravenous heparin administration by an implantable infusion pump in ambulatory patients with recurrent venous thrombosis."Surgery 88:507 (1980).

Campfield et al., 1995, "Recombinant mouse OB protein: evidence for a peripheral signal linking adiposity and central neural networks" Science 269:546-549.

Chen et al. " In Vitro and In Vivo Structure-Activity Relationships of Novel Androgen Receptor Ligands with Multiple Substituents in the B-Ring" Endocrinology, 146(12):5444-54, Dec. 2005.

Chen J, Chung K, Hwang DJ, Miller DD, and Dalton JT. In Vitro Characterization of Novel Selective Androgen Receptor Modulators (SARMs). The Endocrine Society, Philadelphia, Jun. 2003, Abstract #P1-B7.

Chen J, Guan N, Chung K, Miller DD, and Dalton JT. Modulation of Hormonal Biomarkers and Target Organ Weights In Vivo by Selective Androgen Receptor Modulators (SARMs). PharmSci 4(4): 2002.

Chen J, Hwang DJ, Chung K, Nelson R, Miller DD, Dalton JT—In Vitro and In Vivo Characterization of a Selective Androgen Receptor Modulators (SARM). The AAPS Journal, vol. 7(52):T3259, 2005.

Chen J, Hwang DJ, Miller DD, and Dalton JT. A Selective Androgen Receptor Modulator (SARM) for Male Contraception. The Endocrine Society, New Orleans, Abstract # P2-103, Jun. 2004.

Chen J, Xiao J, Chung K, Miller DD, and Dalton JT. Preclinical Pharmacology, Pharmacokinetics, and Metabolism of a Novel Selective Androgen Receptor Modulator (SARM) in Male Rats. The AAPS Journal, vol. 6, No. 4, Abstract #W5299, Nov. 2004.

Considine et al., 1995, "Evidence against either a premature stop codon or the absence of obese gene MRNA in human obesity", J. Clin. Invest. 95:2986-2988.

Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.

Dalton et al., "Therapeutic Promise of Selective Androgen Receptor Modulators (SARSs): Preclinical and Clinical Proof-of-Concept Studies" —The Endocrine Society—Programs and Abstracts—89th Annual Meeting- Paper S41-2 2007.

Dalton JT, et al "Pharmacokinetics of Aminolevulinic Acid after Oral and Intravenous Dosing in Dogs." Drug Metabolism and Disposition, 27 (4):432-435, 1999.

Dalton JT, Mukherjee A, Zhu Z, Kirkovsky L; and Miller DD. Discovery of Nonsteroidal Androgens. Biochemical and Biophysical Research Communications, 244(1): 1-4, 1998.

Dalton JT, Yin D, Perera MA, Gao W, Xu H, Kearbey JD, Chung K, and Miller DD, Preclinical Pharmacology and Pharmacokinetics of a Selective Androgen Receptor Modulator. International Society for Study of Xenobiotics. Drug Metabolism Reviews, 33(supplement 1): #222, 2001.

Diebold SS, Kaisho T, Hemmi H, Akira S, Reis e Sousa C., Innate antiviral response by means of TLR7-mediated recognition of single-stranded RNA, Science Mar. 5, 2004 303(5663):1529-31.

Djerassi and S.P. Leibo, "A new look at male contraception", Nature, vol. 370, pp. 11-12, 1994.

Dukes, "Nonsteroidal progestins and antiprogestins related to flutamide",Steroids. Oct.-Nov. 2000; 65(10-11):725-31.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano [3, 2-g] quinolin-2-one. Bioorg. Med. Chem. Lett., 9: 1003, 1999.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Eliason et al., "High Throughput Fluorescence Polarization-Based Screening Assays for the Identification of Novel Nuclear Receptor Ligands", Abstracts of Papers, 223rd ACS National Meeting, Orlando, FL, United States, (2002), Apr. 7, 2002.

Faulkner KG, et al (1991) "Noninvasive measurements of bone mass, structure, and strength: current methods and experimental techniques." Am J Rosentgenology 157:1229-1237.

Fisher SJ, Hong SS, Miller DD, and Dalton JT. Preclinical Pharmacology and Pharmacokinetics of a Novel A-ring Substituted Selective Androgen Receptor Modulator (SARM) in Rats. The AAPS Journal, vol. 6, No. 4, Abstract #T2256, Nov. 2004.

Fisher SJ, Miller DD, and Dalton JT. Preclinical Pharmacology of A-Ring Substituted Selective Androgen Receptor Modulators (SARMs). PharmSci 5 (4): W524E, 2003.

Francisco, et al., "Long-acting contraceptive agents: testosterone esters of unsaturated acids", Steroids, Jan. 1990, vol. 55, Butterworths.

Gao W, Bohl CE, and Dalton JT. Chemistry and structural biology of androgen receptor. Chemical Reviews, 1G5(9):3352-70,2005.

Gao W, Chung K, Kearbey ID, Miller DD, and Dalton JT. Pharmacologic Effects of Androxolutamide (GTx-007) on Male Rats of Varying Hormonal Status. The Endocrine Society, San Francisco, Jun. 2002.

Gao W, Chung K, Miller DD, and Dalton JT. In Vitro Metabolism and in Vivo Tissue Selectivity of Andarine. PharmSci 4(4): 2002.

Gao W, Coss CC, and Dalton JT. Tissue-Specific Regulation of Transcription Repressor Receptor Ligand (DHT). The Endocrine Society, Boston, Abstract # P3-462, Jun. 2006.

Gao W, Dalton JT, Expanding the therapeutic use of androgens via selective androgen receptor modulators (SARMs). Drug Discovery Today, 12(5-6):241-248, 2007.

Gao W, Dalton JT. Ockham's razor and selective androgen receptor modulators (SARMs): are we overlooking the role of 5a-reductase? Molecular Interventions, 7(1):1Q-13, 2007.

Gao W, Johnston JS, Miller DD, Dalton JT. Inter-Species Differences in Pharmacokinetics and Metabolism of S-3-(4-acelylamino-phenoxy)-2-hydroxy-2-methyl-N-(4-nitro-3-trifluoromethyiphenyl>propionamide: The Role of N-Acetyltransferase. Drug Metabolism and Disposition, 34(2):254260, 2006.

(56) References Cited

OTHER PUBLICATIONS

Gao W, Kearbey JD, Chung K, Miller DD, and Dalton JT. Pharmacologic Effects of a Novel Selective Androgen Receptor Modulator (SARM), Flutamide and Finasteride in Intact Male Rats. The Endocrine Society, Philadelphia, Jun. 2003, Abstract #P3-221.

Gao W, Kim J, Dalton JT, Pharmacokinetics and Pharmacodynamics of Nonsteroidal Androgen Receptor Ligands. Pharmaceutical Research, 23(8):1641-165B, 2006.

Gao W, Reiser PJ, Coss CC, Phelps MA, Kearbey JD, Miller DD, and Dalton JT. Selective Androgen Receptor Modulator (SARM) Treatment Improves Muscle Strength and Body Composition, and Prevents Bone Loss in Orchidectomized Rats. Endocrinology, 146(11):48B74897, 2005.

Gao W, Reiser PJ, Kearbey JD, Phelps MA, Coss CC7 Miller DD, and Dalton JT. Effects of a Novel Selective Androgen Receptor Modulator (SARM) on Skeletal Muscle Mass and Strength in Castrated Male Rats. The Endocrine Society, New Orleans, Abstract # P2-120, Jun. 2005.

Gao W, Stuart LB, Yates CR, Miller DD, and Dalton JT. Regulation of Cytochrome P450s by Selective Androgen Receptor Modulators (SARMs) in Primary Culture of Human Hepatocytes.). PharmSci 5 (4): T3 3 3 8, 2003.

Gao W, Wu Z, Bohl CE, Yang J, Miller DD, Dalton JT. Characterization of the In vitro Metabolism of Selective Androgen Receptor Modulator (SARM) Using Human, Rat and Dog Liver Enzyme Preparations. Drug Metabolism and Disposition, 34(2):243-253, 2006.

Gao W, Wu Z, Chung K, Miller DD, and Dalton JT. Phase I Metabolism Study of Selective Androgen Receptor Modulators (SARMs) with Human Liver Microsomes. PharmSci 5 (4): T3337, 2003.

Gao W, Veverka KA, Chung K, Miller DD, and Dalton JT. Species Difference in the Metabolism of Selective Androgen Receptor Modulators (SARMs). PharmSci 5 (4): T3336, 2003.

Georgian Search Report of Application No. AP 2005 009805 issued on Jan. 23, 2008.

Goldberger NE, Wu Z, and Dalton JT. Using Mass Spectroscopy to Study Ligand-Specific Androgen Receptor (AR) Conformations and Complexes. The Endocrine Society, Boston, Abstract # P3-461, Jun. 2006.

Goodson, in Medical Applications of controlled Release, supra, vol. 2, pp. 115-138 (1984).

Grundy, Metabolic and health complications of obesity, 1990, Disease-a-Month 36:Dec; 36(12):641-731.

Halaas et al., 1995, "Weight-reducing effects of the plasma protein encoded by the obese gene", Science 269:543-546.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210-212, 1999.

Hamilton et al., 1995 "Increased obese mRNA expression in omental fat cells from massively obese humans", Nature Med., 1:953.

Hanada, K., et al (2003) "Bone anabolic effects of S-40503, a novel nonsteroidal selective androgen receptor modulator (SARM), in rat models of osteoporosis." Biol. Pharm. Bull. 26:1563-1569.

Handelsman, "Bridging the gender gap in contraception: another hurdle cleared" The Medical Journal of Australia, vol. 154, Feb. 18, 1996, pp. 230-233.

He Y, Yin D, Perera MA, Kirkovsky L, Stourman N, Dalton JT, and Miller DD. Novel Nonsteroidal Ligands with High Affinity and Potent Functional Activity for the Human Androgen Receptor. European Journal of Medicinal Chemistry, 37: 619-634, 2002.

Heil F, Hemmi H, Hochrein H, Ampenberger F, Kirschning C, Akira S, Lipford G, Wagner H, Bauer S. Species-specific recognition of single-stranded RNA via toll-like receptor 7 and 8, Science Mar. 5, 2004, 303(5663):1526-9.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.

Hoberman and Charles E. Yesalis, "The History of Synthetic Testosterone", Scientific American, Feb. 1995, pp. 76-81.

Hwang DJ, Chen JY, Kim J, Dalton JT, Miller DD. Synthesis and biological testing of (2S)-multU halogenated B-ring 2-hydroxy-2-methylpropionamide selective androgen receptor modulators (SARMs): Probing the B-ring pocket. Abstracts of Papers of the American Chemical Society, 229: U140-U140 176- MEDI Part 2, Mar. 13, 2005.

Hwang DJ, Chen JY, Xu HP, Mustafa SM, Dalton JT, Miller DD. Synthesis of isothiocyanate derivatives of irreversible selective androgen receptor modulators (SARMs) and biological testing in prostate cancer cell lines. Abstracts of Papers of the American Chemical Society, 229: U140-U140 177- Medi Part 2, Mar. 13, 2005.

Hwang DJ, Kim J, Dalton JT, Miller DD. Synthesis and androgen receptor affinity of several linkages of 1,3-disubstituted-2-hydroxy-2-metliylpropionanvide selective androgen receptor modulators (SARMs). Abstracts of Papers of the American Chemical Society, 229: U139-U139 173- Medi Part 2, Mar. 13, 2005.

Hwang DJ, Yang J, Mohler ML, Dalton JT, Miller DD.Synth.esis and testing of both reversible and irreversible selective androgen receptor modulators (SARMs) for prostate cancer. Abstracts of Papers of the American Chemical Society, 231: 274-MEDI, Mar. 26 2006.

Hwang DJ, Yang J, Xu H, Rakov IM, Mohler ML, Dalton JT, Miller DD- Aryl isothiocyanato selective androgen receptor modulators (SARMs) for prostate cancer. Bioorganic and Medicinal Chemistry, 14(19):6525-6538, 2006.

Kalu, DN (1991) "The ovariectomized rat model of postmenopausal bone loss Bone Miner" 15:175-91.

Katre et al. "Chemical modification of recombinant interleukin 2 by polyethylene glycol increases its potency in the murine Meth A sarcoma model" Proc Natl Acad Sci U S A. 84(6):1487-91. Mar. 1987.

Kearbey JD, Chung K, Miller DD, and Dalton JT. Effect of Androxolutamide (GTx-007) on Bone Mineralization in Rats: A Pilot Study. The Endocrine Society, San Francisco, Jun. 2002.

Kearbey JD, Gao W, Miller DD, and Dalton JT. Selective androgen receptor modulators inhibit bone resorption in rats. PharmSci 5 (4): R6167, 2003.

Kearbey JD, Gao W, Narayanan R, Fisher SJ, Wu D, Miller DD, Dalton JT. Selective Androgen Receptor Modulator (SARM) Treatment Prevents Bone Loss and Reduces Body Fat in Ovariectomized Rats. Pharmaceutical Research, 24(2):328-335, 2006.

Kearbey JD, Parke DN, Narayanan R, Okolicany J, Miller DD, and Dalton JT. Preclinical Pharmacology of a Novel Osteoanabolic Tissue Selective Androgen Receptor Modulator. The Endocrine Society, Boston, Abstract # p. 3-64, Jun. 2006.

Kearbey JD, Wu D, Gao W, Chung K, Miller DD, and Dalton JT. Pharmacokinetics of a Nonsteroidal Selective Androgen Receptor Modulator in Rats. PharmSci 4(4): 2002.

Kearbey, J. D., Wu, D., Gao, W., Miller, D. D., and Dalton, J. T. (2004). Pharmacokinetics of S-3-(4-acetylamino-phenoxy)-2-hydroxy-2-methyl-N-(4-nitro-3-trifluoromethyl-phenyl)-propionamide in rats, a non-steroidal selective androgen receptor modulator. Xenobiotica 34(3), 273-80.

Kim J, Hwang DJ, Miller DD, and Dalton JT. Effect of 4-cyano and 4-nitro Substitution on the Pharmacologic Activity and Pharmacokinetics of Selective Androgen Receptor Modulators. The AAPS Journal, vol. $6_7$ No. 4, Abstract #W4118, Nov. 2004.

Kim J, Hwang DJ, Miller DD, and Dalton JT. In vitro and In vivo Pharmacologic Activity of 4-Halo Substituted SARMs. The Endocrine Society, Philadelphia, Jun. 2003, Abstract #P3-198.

Kim J, Hwang DJ, Nair VA, Miller DD, and Dalton JT. Pharmacokinetics of Halogen Substituted SARMs in Rats. PharmSci 5 (4): W5259, 2003.

Kim J, Hwang DJj, Rakov I, Miller DD, and Dalton JT. Structure-Activity Relationships for Modification of the Linkage Group and B-Ring of Selective Androgen Receptor Modulators. The AAPS Journal, vol. 7(S2):T2117, 2005.

(56) References Cited

OTHER PUBLICATIONS

Kim J, Wu D, Hwang DJ, Miller DD, and Dalton JT. The 4-Para-Substituent of S-3-(Phenoxy)-2-hydroxy-2-methyl-N-(4-nitro-3-trifluoromethy-phenyl)-propionamides is a Major Structural Determinant of In Vivo Disposition and Activity of Selective Androgen Receptor Modulators. Journal of Pharmacology and Experimental Therapeutics, 315(D:230-239, 2005.
Kirkovsky et al., "Approaches to Irreversible non-steroidal chiral antiandrogen", Department of Pharmaceutical Sciences, University of Tennessee, 47th Southeast/51st Southeast Joint Regional Meeting of the American Chemical Society, Memphis, TN, Nov. 29-Dec. 1, 1995.
Kirkovsky L, Mukherjee A, Dalton JT, and Miller DD. Chiral Non-Steroidal Antiandrogen Analogs of Hydroxyflutamide. National. Amer. Chem. Soc. Mtg., New Orleans, LA, 1996.
Koski GK, Kariko K, Xu S, Weissman D, Cohen PA, Czerniecki BJ, Cutting edge: innate immune system discriminates between RNA containing bacterial versus eukaryotic structural features that prime for high-level IL-12 secretion by dendritic cells, J. Immunol. Apr. 1, 2004 172(7):3989-93.
Laaksonen et al. " Sex hormones, inflammation and the metabolic syndrome: a population-based study" European Journal of Endocrinology, vol. 149, Issue 6, 601-608, Dec. 2003.
Langer, "New methods of drug delivery", Science 249:1527-1533(1990).
Langer, et al (1987) " "Crc Crit. Ref. Biomed. Eng. 14;201.
Lemus AE et al, "5alpha-reduction of norethisterone enhances its binding affinity for androgen receptors but diminishes its androgenic potency" J. Steroid. Biochem. Mol. Biol. 60(1-2): 121-9, Jan. 1997.
Lonnquist et al., 1995, Nature Med. 1:950.
McKillop, et al., "Enantioselective metabolism and pharmacokinetics of Casodex in the male rat", Xenobiotica, 1995, vol. 25, No. 6, 623-634.
Miller DD, Brueggemeier RW, and Dalton JT. Sex Hormones. In: Principles of Medicinal Chemistry, 5th Edition. Foye WO, Lemfce TI, and Williams DA (Eds.), Williams and Wilkins, Baltimore, MD. 2001.
Miller DD, Stourman N, Kirkovsky L, Zhu Z, and Dalton JT. Chiral Epoxides as Irreversible Probe for the Androgen Receptor. National Amer, Chem. Soc. Mtg., Las Vegas, NV, MEDI-222, 1997.
Mukherjee A, Kimura Y, Kirkovsky L, Miller DD, and Dalton JT. Alkylation of the Androgen Receptor with Nonsteroidal Affinity Ligands and Determination of their Functional Activity. Pharmaceutical Res., 14(11):5393, 1997.
Mukherjee A, Kirkovsky L, Miller DD, and Dalton JT. In Vitro Pharmacologic Characterization of Nonsteroidal Affinity Ligands for the Androgen Receptor. Pharmaceutical Res., 13(9):5491, 1996.
Mukherjee A, Kirkovsky L, Yao XT, Yates CC, and Dalton JT. Enantioselective Binding of Casodex to the Androgen Receptor. Xenobiotica 26(2): 117-122, 1996.
Nair V, Mustafa SM, Mohler ML, Fisher S J, Dalton JT, and Miller DD. Synthesis of irreversibly binding bicalutamide analogs for imaging studies. Tetrahedron Letters. 46:4821-4823, 2005.
Nair VA, Mustafa SM3 Mohler ML, Fisher SJ, Dalton JT, and Miller DD. Synthesis of Novel Iodo Derived Bicalutamide Analogs. Tetrahedron Letters, 45: 9475-9477, 2004.
Nair VA; Mustafa SM; Mohler ML; Dalton JT; Miller DD.Synthesis of oxazolidinedione derived bicalutamide analogs. Tetrahedron Letters, 47 (23): 3953-3955, 2006.
Narayanan et al., "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society- Programs and Abstracts-89th Annual Meeting- Paper P1-595 2007.
Narayanan R, Bohl CE, Kearbey JD, Coss CC, Miller DD, and Dalton JT. Molecular Mechanism for the Tissue Selectivity of a Novel Non-Steroidal Selective Androgen Receptor Modulator: Genome-Wide Mapping of Androgen Receptor Binding Sites, The Endocrine Society, Boston, Abstract # OR49-1, Jun. 2006.

Narayanan R, Coss CC, Yepuru MM, Miller DD and Dalton JT. Steroidal Androgens and Nonsteroidal, Tissue Selective Androgen Receptor Modulators (SARM) Regulate Androgen Receptor Function Through Distinct Genomic and Non-Genomic Signaling Pathways. The Endocrine Society, Toronto, Abstract #PI-595, Jun. 2007.
Negro-Vilar, A. (1999) "Selective androgen receptor modulators (SARMs): a novel approach to androgen therapy for the new illennium." J. Clin. Endocrin Metabol. 84: 3459-3462.
Patil R, Li W, Ross CR, Kraka E, Cremer D, Mohler ML, Dalton JT, and Miller DD. Cesium fluoride and tetra-n-butylammonium fluoride mediated 1,4-N-O shift of disubstituted phenyl ring of a bicalutamide derivative. Tetrahedron Letters, 47:3941-3944, 2006.
Pelleymounter et al., 1995, "Effects of the Obese gene product on body weight regulation in ob/ob mice", Science 269:540-543.
Perera MA, Yin D, Chung K, Chan KK, Miller DD, and Dalton JT. Metabolism of a Novel Selective Androgen Receptor Modulator. PharmSci 5 (4): T3360, 2003.
Perera MA, Yin D, Chung K, Miller DD, and Dalton JT. Pharmacokinetics and Allometric Scaling of Andarine. PharmSci 4(4): 2002.
Perera MA, Yin D, Chung K, Miller DD, and Dalton JT. Pharmacokinetics of androxolutamide (GTx007) in beagle dogs. The Endocrine Society, San Francisco, Jun. 2002.
Press B, Snyder L, Reust M, Dalton JT, Yuan DZ, Veverka KA. In vitro metabolic profile of novel nonsteroidal selective androgen receptor modulators. Drug Metabolisms Reviews, 38: 92-93 146 Suppl. 2, 2006. International Society for the Study of Xenobiotics, Puerto Rico. Oct. 2006.
Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.
Saudek et al."A preliminary trial of the programmable implantable medication system for insulin delivery." N. Engl. J. Med. 321:574 (1989).
Saudek, et al A preliminary trial of the programmable implantable medication system for insulin delivery. N. Engl J Med. Aug. 31, 1989; 321(9):574-9.
Sefton, "Implantable pumps" CRC Crit. Ref. Biomed. Eng. 14:201 (1987).
Segal S, Narayanan R, Dalton JT. Therapeutic potential of the SARMs: revisiting the androgen receptor for drug discovery. Expert Opinion in Investigational Drugs. 15(4):377-87, 2006.
Sharifi N, Hamel E, Lill MA, Risbood P, Kane CT Jr, Hossain $MT_3$ Jones A, Dalton JT, Farrar WL. A bifunctional colchicinoid that binds to the androgen receptor. Molecular Cancer Therapeutics, 6(8):2328-2336, 2007.
Singh et al., "Androgens stimulate myogenic differentiation and inhibit adipogenesis in C3H 10T1/2 pluripotent cells through an androgen receptor-mediated pathway" Endocrinology,144(11):5081-8, Jul. 24, 2003.
Staiman and Lowe "Tamoxifen for Flutamide/Finasteride-Induced Gynecomastia" Urology, 1997, 50: 929-933.
Steinberger et al., Effect of chronic Administration of Testosterone Enanthateon Sperm Production and Plasma Testosterone, Follicle Stimulating Hormone, and Luteinizing Hormone Levels: a Preliminary Evaluation of possible Male Contraceptive, Fertility and Sterility 28:1320-28 (1977).
Sundaram et al. "7α-Methyl-Nortesterone (Ment): The Optimal Androgen for Male Contraception" Ann Med 1993;25: 199-205.
Supplementary European Search Report of Application No. EP 05 75 8756 issued on May 29, 2008.
Terashima, et al (1979) "Asymmetric Halolactonsation Reaction-1" Tetrahedron Letters vol. 35 2337-2343.
Treat et al., in Liposomes in the Therapy of infections disease and cancer, Lopez-Berestein and Fidler (eds.), Liss New York, pp. 353-365 (1989).
Tucker and Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer ".

(56) References Cited

OTHER PUBLICATIONS

Tucker et al "Nonsteroidal antiandrogens. Synthesis and structure-activity relationships of 3-substituted derivatives of 2-hydroxypropionanilides." J. Med Chem (1988), 31, 954-959.

Vippagunta et al., "Crystalline Solids", Advanced Drug Delivery Reviews, vol. 48, No. 1; pp. 326, 2001.

Wahner H W et al., "Assesment of Bone Mineral Part 1", J Nucl Medicine, pp. 1134-1141 (1984).

Wahner H W et al., "Bone Mineral Density of the Radius", J Nucl Medicine, 26:13-39 (1985).

Wang L, Miller DD, and Dalton JT, Androgen Receptor Mediated Transcriptional Activation of SARMs is Enhanced by Nuclear Receptor Coactivators. The Endocrine Society, Philadelphia, Jun. 2003, Abstract #P2-95.

Watkins "Cardiovascular disease, hypertension, and lipids" Clinical Review, BMJ, vol. 326, Apr. 2003, pp. 874-876.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.

World Health Organization Task Force on Methods and Regulation of Male Fertility "Contraceptive Efficacy of Testosterone-Induced Azoospermia and Oligospermia in Normal Men", Fertility & Sterility 65:821-29 (1996).

Wright C et al, "Analysis of myosin heavy chain mRNA expression by RT-PCR", J. Appl. Physiol. Oct. 1997; 83(4): 1389-96.

Wu D, Gao W, Kearbey JD, Chung K, Miller DD, and Dalton JT. Phaimacokinetics of a selective androgen receptor modulator (SARM), S-I, in rats. PharmSci 5 (4): W5267, 2003.

Wu D, Miller DD, and Dalton JT. Electrospray LC/MS method using single-ion monitoring and a monolithic silica column for quantitation and preclinica pharmacokinetics of a novel selective androgen receptor modulator (SARM) in rats. American Society of Mass Spectrometry, Montreal, Canada, Jun. 2003.

Wu D, Wu Z, Nair V, Miller DD, and Dalton JT- Urinary Metabolites of S-I, A Novel Selective Androgen Receptor Modulator (SARM), in Rats. The AAPS Journal, vol. 6, No. 4, Abstract #W53OO, Nov. 2004.

Wu D, Wu Z, Yang J, Nair VA, Miller DD, Dalton JT. Pharmacokinetics and metabolism of a selective androgen receptor modulator (SARM) in rats-implication of molecular properties and intensive metabolic profile to investigate ideal pharmacokinetic characteristics of a propanamide in preclinical study. Drug Metabolism and Disposition, 34(3):483-494, 2006.

Wu Z, Bohl CE, Goldberger N, Miller DD, and Dalton JT. Peptide mapping of the human androgen receptor ligand-binding domain using mass spectrometry. American Society of Mass Spectrometry, Montreal, Canada, Jun. 2003.

Wu Z, Gao W, Phelps M, Wu D, Miller DD, and Dalton JT. The Favorable Effects of Weak Acids on Negative-Ion Electrospray Mass Spectrometry. Analytical Chemistry, 76(3):839-847, 2004.

"Effects of Testosterone Enanthate in Normal Men: Experience from a Multicenter contraceptive efficacy study", Fertility and Sterility 65:626-36 (1996).

Wu, "Male Contraception: Current Status and Future Prospects", Clinical Endocrinology, (1988), 29, pp. 443-465.

Xu H, Chung K, Hwang DJ, Miller DD, and Dalton JT. Pharmacodynamics of Electrophilic Androgen Receptor Ligands in Prostate Cancer Cell Lines. PharmSci 4(4): 2002.

Xu H, Hwang DJ, Miller DD, and Dalton JT. In Vitro and In Vivo Anticancer Activity of S-NTBA for Prostate Cancer. PharmSci 5 (4): T2378, 2003.

Yang J, Bohl CE, Nair VA, Mustafa SM, Hong SS, Miller DD, Dalton JT. Preclinical pharmacology of a nonsteroidal ligand for androgen receptor mediated imaging of prostate cancer. Journal of Pharmacology and Experimental Therapeutics, 317(I):402-408, 2006.

Yepuru, et al "An Angrogen Receptor-b Specific Selective Estrogen Receptor Modulator (SERM) Inhibits the Growth of the Prostate Cancer Cells and Stromal-Epithilial Tumor Xenograft." The Endocrine Society—Programs and Abstracts—89th Annual Meeting—Paper OR6-3. 2007.

Yin D, Gao W, Kearbey JD, Xu H, Chung K, Miller DD, and Dalton JT. Pharmacodynamics of Selective Androgen Receptor Modulators. Journal of Pharmacology and Experimental Therapeutics, 304(3): 1334-1340, 2003.

Yin D, He Y, Xu H, Miller DD, and Dalton JT. Metabolism of (R)-Para-Acetamido Bicalutamide in Rats. PharmSci 2(4):2000.

Yin D, Kirkovsky L, Stourman N, Miller DD, and Dalton JT. In Vitro Pharmacology and In Vivo Pharmacokinetics of (R)-Para-Acetamido-Bicalutamide. PharmSci, 1(4):S-3185, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Zhou et al., Molec. Endocrinol. 9: 208-18 (1995).

Zilbermint et al., "Nonsteroidal selective androgen receptor modulator Ostarine in cancer cachexia", Future Oncol. (2009) 5(8), pp. 1211-1220.

Supplementary European Search Report for European Application No. 11732323.8.

* cited by examiner

METHODS OF TREATING MEIBOMIAN GLAND DYSFUNCTION

CROSS-REFERENCE TO RELATED APPLICATIONS

This Application claims priority from U.S. Provisional Application Ser. No. 61/293,966, filed Jan. 11, 2010 which is hereby incorporated by reference in its entirety.

FIELD OF THE INVENTION

The present invention includes methods for treating Meibomian gland dysfunctions. The invention also includes methods for improving tear lipid composition, for treating abnormal Meibomian gland secretion and for normalizing Meibomian gland secretions.

BACKGROUND OF THE INVENTION

Meibomian glands are a type of sebaceous gland (i.e. holocrine glands) located in the tarsal plate of the upper and lower eyelids. These glands are responsible for the supply of sebum, an oily substance that prevents evaporation of the eye's tear film, prevents tear spillage onto the cheek, and makes the closed lids airtight. There are approximately 50 glands on the upper eyelids and 25 glands on the lower eyelids. Meibomian glands are distinguished by grape-like clusters of acini on the mucocutaneous lid junction, and empty their lipid content (sebum) at this junction in order to coat the ocular surface via holocrine breakdown. The glands are anchored by cells that produce both polar and nonpolar lipids, which are then stored in lysosomes that merge into larger storage granules. As these cells continue to enlarge with lipid, they eventually rupture into the meibomian gland opening and spill the sebum over the ocular surface. These lipids are liquid at room temperature, typically with a melting point of between about 66 and 89° F., and are distributed over the ocular surface in a thin, smooth film called meibum. This meibum functions to prevent evaporation of the aqueous layer. Alterations in the meibum composition can have a profound effect on the health of the eyelid margins and ocular surface. Dysfunction of Meibomian glands in the general population is pretty high with some estimates as high as 39% (see, e.g., Hom M M et. al. *Optom Vis Sci.*, 67(9), 710-2, 1990) with an increase in incidence in contact lens wearers (see, e.g., Ong B L. *Optom Vis Sci.*, 73(3), 208-10, 1996).

Meibomian gland secretions form the lipid layer of tears and consist of polar and nonpolar lipids. The lipid type as well as fatty acid and alcohol composition of the meibum can affect tear parameters like initial formation of a composite monolayer with polar and nonpolar phases, adequate fluidity near body temperature, and the ability to undergo compression and expansion during blinking (see, e.g., McCulley et al., *Adv Exp Med. Biol.*, 506 (Pt A), 373-8, 2002). In the human tear film lipid bilayer, the polar-phase lipids contain fatty acids with carbon chain lengths of 14-18 (C14-18) that are normally saturated. These properties are very important for effective polar lipid structuring and fluidity (melted physical state) at normal body temperature (see, e.g., McCulley et al., *Adv Exp Med. Biol.*, 506(Pt A):373-8, 2002). Any alterations in the saturation of the fatty acids can lead to instability in the polar phase of lipids and thereby to instability of tears. In conditions like blepharitis that lead to meibomian gland dysfunction the normal fatty acid profile sometimes trends toward greater unsaturation. Any drug that can improve levels of saturated fatty acid would be beneficial to the treatment of meibomian gland disease.

Common complaints of patients suffering from Meibomian gland dysfunction include blurred or filmy vision, especially after performing near tasks, burning or foreign body sensations in the eye, excessive tearing, intolerance to contact lens, photophobia, and pain severe enough to awaken the person from sleep. Although patients with this condition usually have normal production of aqueous tears by their lacrimal glands, their Meibomian glands can atrophy and this is frequently accompanied by metaplasia of the ductal epithelium of these glands. Anterior erosion of the mucocutaneous junction of the eyelid is often noted, as well as eyelid and conjunctival infection, eyelid margin irregularity, corneal epithelial changes, and corneal vascularization. Common clinical tests to evaluate Meibomian gland dysfunction include Schirmer tear test, fluorescein staining (also known as ocular staining or conjunctival staining), and tear film break up time (TFBUT), each of which is briefly described below.

Schirmer tear test (STT): The Schirmer tear test is a measure of aqueous tear production. It is a clinical parameter used for dry eye and is done in normal or anesthetized eyes of patients to evaluate basal and reflex tearing. STT is performed by using standardized strips of filter paper with or without an impregnated dye and millimeter increments. The ends of the filter paper are placed in the conjuctival formix of each eye and amount of tears produced over one minute is measured. STT readings vary between species of animals. In dog it is typically greater than 10 mm of wetting/minute. Often in chronic Meibomian gland dysfunction the corneal epithelium shows significant dye uptake.

Fluorescein staining (a.k.a. ocular staining or conjunctival staining): This test is used to measure corneal epithelium integrity. Fluorescein dye is applied to the eye can be applied as a drop. Immediately after application of the dye, the patient is either allowed to blink or the eyelids are closed and opened manually. The excess fluorescein is then washed with eyewash and the corneal surface is then examined in a dark room with a cobalt blue filter fitted to a direct ophthalmoscope. Any uptake of the dye to the cornea is indicative of a disruption in the corneal surface epithelium. Often in chronic Meibomian gland dysfunction the corneal epithelium shows significant dye uptake.

Tear film break up time (TFBUT): This test is a subjective measure of precorneal tear film stability. TFBUT measures the time taken for the tears to evaporate from the surface of the cornea. In this test fluorescein dye is applied to the cornea and dye is allowed to pool on the cornea. Eyelids are opened and closed manually while eye examination is done with the blue light from cobalt blue fitted direct ophthalmoscope. The time taken from opening of the eyelids (formation of the green film on cornea) to the first appearance of a black area within the green stain of the cornea is measured. In humans TFBUT is typically less than 5 secs. In dogs it is 20 seconds. TFBUT is considered abnormal if the TFBUT is less than 3 secs in humans and less than 10 secs in dogs. Often in chronic Meibomian gland dysfunction the TFBUT is significantly decreased.

As Meibomian glands lining the eyelids produce lipids that promote the stability of the tears and reduce evaporation of the tear film, dysfunction of the Meibomian glands can lead to lipid insufficiency that destabilizes the tear film and causes decreases in tear film break-up time and evaporative dry eye (see, e.g., Sullivan et al., *Ann. NY Acad. Sci.*, 966, 211-222, 2002).

Meibomian gland dysfunction may also be characterized by increased melting point of the lipids, causing solidification of the lipids and obstruction of the Meibomian gland secretion. This can result in cysts, infections and decreased lipid content in the tears. Meibomian gland dysfunction is also characterized by excess, abnormally turbid secretion that gets inspissated and plugs the meibomian orifices. This is followed by metaplasia of the meibomian ducts (abnormal keratinization). Blockage and resistance to flow results in inflammation and vascularization (redness) of tissue around the orifice. Inflammatory mediators accumulate in the tear film leading to damage of ocular surface. Sequlae of all these events is inflammatory scarring of the duct leading to stenosis. Initially glands swell and eventually atrophy.

Commonly used treatments include warm compresses to eyelid margins, mechanical probing of meibomian ducts, using infrared devices or chemicals to eyelid margins to induce tear lipid melting and secretion. For inflammation, glucocorticoids are used. If there is a bacterial component, antibiotics like penicillin, doxycycline and tetracyclines are used.

The physiology of the Meibomian gland function is believed to be under the control of androgens. Conditions of androgen deficiency that occur during aging, menopause, and androgen deprivation therapy for prostate cancer have been associated with evaporative dry eye (see, e.g., Sullivan et. al., *Ann. NY Acad. Sci.*, 966, 211-222, 2002) indicating that androgens may play a major part in the etiology of this condition. Administration of 19-nortestosterone modulated the fatty acid profile in total and neutral lipid fractions in Meibomian gland secretions of rabbits (see, e.g., Sullivan et al., *IOVS*, 41(12), 3732-3742, 2000) indicating that androgen supplementation could be of benefit in treating such conditions.

Systemic androgen therapy with traditional steroidal agents is, however, associated with several undesirable side effects, including acne, seborrhea, hirsutism and concerns regarding prostate enlargement. The ability of 5α-reductase inhibitors to promote hair growth (topical) and treat prostatic disease (systemic) suggests that dihydrotestosterone (DHT), a potent full agonist for the androgen receptor and metabolite of testosterone, may be responsible for many of these virilizing effects.

Previous treatments of Meibomian gland dysfunctions were typically directed only to treatment of presumed infection of the eyelids or Meibomian glands, or had particular disadvantages that made such treatments of little use for long periods of time. For example, patients with Meibomian gland dysfunctions have been symptomatically treated with artificial tears, but these agents provide limited, if any, improvement. Topically applied glucocorticoids to the eyelids or ocular surface are effective as short-term pulse therapies. However, glucocorticoids are not good long-term solutions because of the potential side-effects e.g., cataract and glaucoma. Meibomian gland dysfunction is currently not curable or reversible; therefore, patients with this condition must be treated for life.

Hence, there is a need in the art to develop new methods of treating Meibomian gland dysfunctions. Applicants have developed compounds that provide a unique treatment approach for Meibomian gland dysfunction due to their ability to promote lipid production, lack of virilizing effects, and tissue selectivity. The methods described herein provide effective treatment for Meibomian gland dysfunctions with less undesirable side effects.

SUMMARY OF THE PRESENT INVENTION

In one embodiment, this invention provides a method of treating a Meibomian gland dysfunction, comprising administering to a subject in need thereof a compound as described herein.

In other embodiments, this invention provides methods of improving tear lipid composition, comprising administering to a subject in need thereof a compound as described herein.

In additional embodiments, the present invention also relates to the following methods: improving tear lipid composition, increasing tear lipid content, increasing tear fatty acid content, increasing tear palmitate:stearate ratios, treating abnormal Meibomian gland secretions, preventing Meibomian gland dysfunction, treating and preventing dry eye, normalizing Meibomian gland secretions, decreasing Meibomian gland secretion viscosity, increasing Meibomian gland secretion transparency, decreasing the phase transition temperature of lipids in the tears, decreasing the number of plugged and/or obstructed Meibomian glands, reducing the redness of the eyelid margins, reducing burning and/or itching in a subject's eye, reducing the need of administration of artificial tears to a subject's eye, reducing the requirement of steroid therapy to an eye, decreasing the sensation of a foreign body in a subject's eye, decreasing the time (refractory period) between Meibomian gland secretions, reducing ocular discomfort, increasing tear film break-up time, reducing corneal epithelial erosion, reducing aqueous tear deficiency, reducing ocular and conjunctival staining, and reducing blurred and/or fuzzy vision, comprising administering to a subject in need thereof a compound as described herein.

In additional embodiments of any method described herein, the subject is a mammal. In one embodiment of any method described herein, the subject is a human. In other embodiments of any method described herein, the subject is a domestic animal (e.g., cat, dog).

DETAILED DESCRIPTION OF THE PRESENT INVENTION

Figure 1:
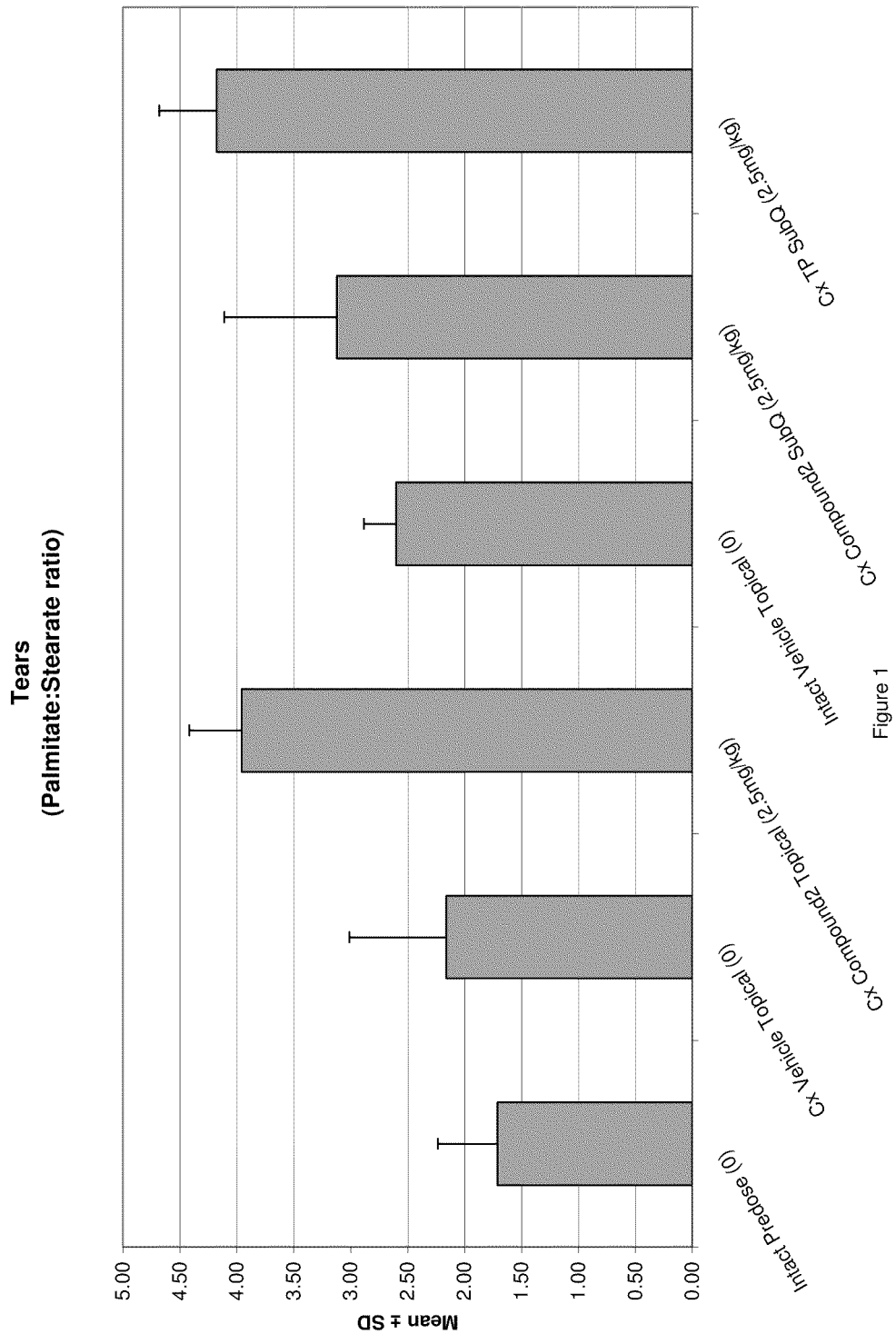
FIG. 1 depicts the tear fatty acid composition in response to the drug treatment described in Example 3.

In one aspect, the present invention relates to methods of treating a Meibomian gland dysfunction. The methods involve administering a selective androgen receptor modulator (SARM) compound.

Thus, in one embodiment, this invention provides a method of treating a Meibomian gland dysfunction, comprising administering to a subject in need thereof a compound of Formula I:

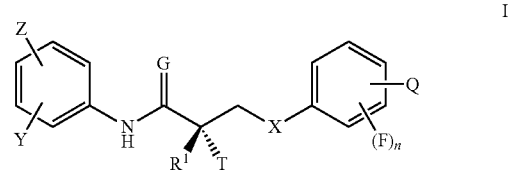

wherein
X is O or S;
G is O or S;
Z is $NO_2$ or CN;
Y is halogen or $CF_3$;
Q is halogen, NHCOR or CN;
T is OH, OR or NHCOR;

R is alkyl, aryl, alkenyl, halogen or OH;
$R^1$ is $CH_3$, $CF_3$, $CH_2F$, $CHF_2$, $CH_2CH_3$ or $CF_2CF_3$; and
n is 0 or 1;
or a prodrug, isomer, metabolite, pharmaceutically acceptable salt, polymorph, crystal, N-oxide, pharmaceutical product, hydrate, or any combination thereof.

In certain embodiments, the methods of this invention make use of a compound of formula I. In one embodiment X of formula I is O. In another embodiment X of formula I is S. In another embodiment G of formula I is O. In another embodiment G of formula I is S. In another embodiment Z of formula I is $NO_2$. In another embodiment Z of formula I is CN. In another embodiment Q of formula I is CN. In another embodiment Q of formula I is F. In another embodiment Q of formula I is Br. In another embodiment Q of formula I is Cl. In another embodiment Q of formula I is I (iodine). In another embodiment T of formula I is OH. In another embodiment $R^1$ of formula I is $CH_3$.

In additional embodiments, any of the methods described herein comprise administering:

Compound 1

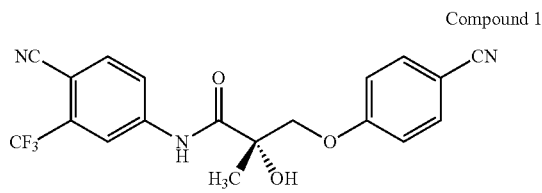 [SMILES: C[C@](O)(COc1ccc(C#N)cc1)C(=O)Nc1ccc(C#N)c(C(F)(F)F)c1]

or a prodrug, isomer, metabolite, pharmaceutically acceptable salt, pharmaceutical product, polymorph, crystal, N-oxide, hydrate, or any combination thereof.

In further embodiments, any of the methods described herein comprise administering:

Compound 2

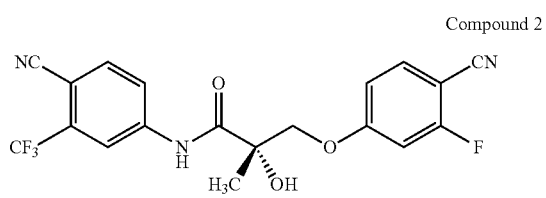 [SMILES: C[C@](O)(COc1ccc(C#N)c(F)c1)C(=O)Nc1ccc(C#N)c(C(F)(F)F)c1]

or a prodrug, isomer, metabolite, pharmaceutically acceptable salt, pharmaceutical product, polymorph, crystal, N-oxide, hydrate or any combination thereof.

In certain embodiments, any of the methods described herein comprise administering:

Compound 3

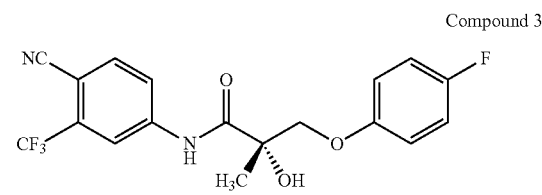 [SMILES: C[C@](O)(COc1ccc(F)cc1)C(=O)Nc1ccc(C#N)c(C(F)(F)F)c1]

or a prodrug, isomer, metabolite, pharmaceutically acceptable salt, pharmaceutical product, polymorph, crystal, N-oxide, hydrate, or any combination thereof.

Thus, in one embodiment, this invention provides a method of treating a Meibomian gland dysfunction, comprising administering to a subject in need thereof a compound as described in any embodiment herein.

In one embodiment, this invention provides a method of preventing a Meibomian gland dysfunction, comprising administering to a subject in need thereof a compound as described in any embodiment herein. In another embodiment, methods of preventing the recurrence of, suppressing, inhibiting or reducing the incidence of Meibomian gland dysfunction in a subject comprising administering to a subject in need thereof a compound as described in any embodiment herein.

In one embodiment, this invention provides a method of treating or preventing dry eye, comprising administering to a subject in need thereof a compound as described in any embodiment herein. In another embodiment, methods of preventing the recurrence of, suppressing, inhibiting or reducing the incidence of dry eye in a subject comprising administering to a subject in need thereof a compound as described in any embodiment herein.

In additional embodiments, the Meibomian gland dysfunction is sometimes associated with blepharitis, posterior blepharitis, keratitis, punctuate keratitis, ocular infections, sties, chalazia or ocular rosacea.

In another embodiment, the present invention relates to methods for improving tear film break-up time (TFBUT), comprising administering to a subject in need thereof a compound as described herein. In another embodiment, the present invention relates to methods for altering tear film break-up time (TFBUT), comprising administering to a subject in need thereof a compound as described herein. In certain embodiments, the tear film break-up time is increased. In other embodiments, the tear film break-up time is decreased.

In another embodiment, the present invention relates to methods for increasing volume of tears (as measured by Schirmer tear test), comprising administering to a subject in need thereof a compound as described herein.

In another embodiment, the present invention relates to methods for reducing, improving and/or preventing foreign body sensation, itching, ocular pain and/or redness of eyes, comprising administering to a subject in need thereof a compound as described herein.

In another embodiment, the present invention relates to methods for reducing, improving and/or preventing inflammation of corneal surface due to excessive drying, comprising administering to a subject in need thereof a compound as described herein.

In another embodiment, the methods described herein alter tear lipid composition. In another embodiment, the methods described herein improve tear lipid composition. Thus, in another embodiment, the present invention relates to methods of altering tear lipid composition comprising administering to a subject in need thereof a compound as described in any embodiment herein. In another embodiment, the present invention relates to methods of improving tear lipid composition comprising administering to a subject in need thereof a compound as described in any embodiment herein. In another embodiment, the present invention relates to methods of decreasing tear lipid content comprising administering to a subject in need thereof a compound as described in any embodiment herein.

In additional embodiments, the improvement in tear lipid composition comprises increasing the tear fatty acid content. In additional embodiments, the improvement in tear lipid composition comprises decreasing the tear lipid content. In additional embodiments, the improvement in tear lipid composition comprises increasing the tear palmitate:stearate ratio. In additional embodiments, the improvement in tear lipid composition comprises decreasing the melting point of lipids in the tears.

In further embodiments, the present invention relates to methods for treating an abnormal Meibomian gland secretion, comprising administering to a subject in need thereof a compound as described in any embodiment herein.

In yet further embodiments, the present invention relates to methods for normalizing a Meibomian gland secretion, comprising administering to a subject in need thereof a compound as described in any embodiment herein.

In one embodiment, the present invention relates to methods for decreasing Meibomian gland secretion viscosity, comprising administering to a subject in need thereof a compound as described in any embodiment herein.

In another embodiment, the present invention relates to methods for increasing Meibomian gland secretion transparency, e.g., in one embodiment, to a colorless state, comprising administering to a subject in need thereof a compound as described in any embodiment herein.

In another embodiment, the present invention relates to methods for altering the phase transition temperature of lipids in tears, comprising administering to a subject in need thereof a compound as described in any embodiment herein. In certain embodiments, the phase transition temperature of lipids in tears is decreased.

In one embodiment, the present invention relates to methods for increasing the palmitate to stearate ratio of lipids in tears, comprising administering to a subject in need thereof a compound as described in any embodiment herein.

In another embodiment, the present invention relates to methods for decreasing the phase transition temperature of lipids in tears, comprising administering to a subject in need thereof a compound as described in any embodiment herein In another embodiment, the present invention relates to methods for decreasing plugging and/or obstruction of Meibomian glands, comprising administering to a subject in need thereof a compound as described in any embodiment herein. In one embodiment, the present invention relates to methods for decreasing the number of plugged and/or obstructed Meibomian glands, comprising administering to a subject in need thereof a compound as described in any embodiment herein.

In another embodiment, the present invention relates to methods for reducing the redness of the eyelid margins, comprising administering to a subject in need thereof a compound as described in any embodiment herein. In one embodiment, the reduction in redness is measured photometrically. In one embodiment, the reduction in redness is measured visually.

In another embodiment, the present invention relates to methods for reducing burning and/or itching in an eye, comprising administering to a subject in need thereof a compound as described in any embodiment herein.

In another embodiment, the present invention relates to methods for reducing the need for adding artificial tears to an eye, comprising administering to a subject in need thereof a compound as described in any embodiment herein.

In another embodiment, the present invention relates to methods for reducing the requirement of steroid therapy to an eye, comprising administering to a subject in need thereof a compound as described in any embodiment herein.

In another embodiment, the present invention relates to methods for reducing the frequency of administration of artificial tears to an eye, comprising administering to a subject in need thereof a compound as described in any embodiment herein.

In another embodiment, the present invention relates to methods for decreasing the sensation of a foreign body in an eye, comprising administering to a subject in need thereof a compound as described in any embodiment herein.

In another embodiment, the present invention relates to methods for decreasing the time (refractory period) between Meibomian gland secretions, comprising administering to a subject in need thereof a compound as described in any embodiment herein.

In additional embodiments, the present invention relates to methods for reducing ocular discomfort, comprising administering to a subject in need thereof a compound as described in any embodiment herein.

In additional embodiments, the present invention relates to methods for increasing tear film break-up time, comprising administering to a subject in need thereof a compound as described in any embodiment herein.

In additional embodiments, the present invention relates to methods for increasing tear-film stability, comprising administering to a subject in need thereof a compound as described in any embodiment disclosed herein.

In additional embodiments, the present invention relates to methods for reducing corneal epithelial erosion as seen with fluorescein staining, comprising administering to a subject in need thereof a compound as described in any embodiment herein.

In additional embodiments, the present invention relates to methods for reducing aqueous tear deficiency, comprising administering to a subject in need thereof a compound as described in any embodiment herein.

In additional embodiments, the present invention relates to methods for reducing blurred and/or fuzzy vision, comprising administering to a subject in need thereof a compound as described in any embodiment herein.

In additional embodiments, the methods described herein improve a subject's reading on a Schirmer test. In one embodiment, the methods increase the number of millimeters a subject's tears wet a paper test strip during a Schirmer test.

In one embodiment, the methods of the invention comprise administering a compound as described in any embodiment herein, or a prodrug, isomer, metabolite, pharmaceutically acceptable salt, pharmaceutical product, polymorph, crystal, N-oxide, hydrate or any combination thereof. In other embodiments, the methods of the invention comprise administering a compound as described in any embodiment herein, or an isomer, metabolite, pharmaceutically acceptable salt, pharmaceutical product, polymorph, N-oxide, hydrate or any combination thereof. In other embodiments, the methods of the invention comprise administering a compound as described in any embodiment herein, or an isomer, pharmaceutically acceptable salt, pharmaceutical product, polymorph, N-oxide, hydrate or any combination thereof. In other embodiments, the methods of the invention comprise administering a compound as described in any embodiment herein, or an isomer, pharmaceutically acceptable salt, pharmaceutical product, N-oxide, hydrate or any combination thereof. In other embodiments, the methods of the invention comprise administering a compound as described in any embodiment herein, or an isomer, pharmaceutically acceptable salt, or any combination thereof.

In other embodiments, the methods of the invention comprise administering an isomer of a compound as described herein. In other embodiments, the methods of the invention comprise administering a metabolite of a compound as described herein. In other embodiments, the methods of the invention comprise administering a pharmaceutically acceptable salt of a compound as described herein. In other embodiments, the methods of the invention comprise administering a hydrate of a compound as described herein. In other embodiments, the methods of the invention comprise administering an N-oxide of a compound as described herein. In other embodiments, the methods of the invention comprise administering a pharmaceutical product of a compound as described herein. In other embodiments, the methods of the invention comprise administering a prodrug of a compound as described herein. In other embodiments, the methods of the invention comprise administering a polymorph of a compound as described herein. In other embodiments, the methods of the invention comprise administering a crystal of a compound as described herein.

One of ordinary skill in the art will recognize that some compounds useful in the methods disclosed herein can exist in different tautomeric and/or geometrical isomeric and/or optical isomeric forms. All of these forms, including cis isomers, trans isomers, diastereomic mixtures, racemates, non-racemic mixtures of enantiomers, substantially pure, and pure enantiomers, are within the scope of the present invention. Substantially pure enantiomers contain, e.g., no more than 5% w/w of the corresponding opposite enantiomer, such as no more than 2% or no more than 1%.

In one embodiment, the term "isomer" is meant to encompass optical isomers of the compound. In one embodiment, the term "isomer" is meant to encompass stereoisomers of the compound. It is to be understood that the present invention encompasses any optically-active, or stereroisomeric form, or mixtures thereof, and use of these for any application is to be considered within the scope of this invention.

In one embodiment, the compounds useful in the methods described herein are substantially pure (R)-isomers. In another embodiment, the compounds useful in the methods described herein are substantially pure (S)-isomers. In another embodiment, the compounds useful in the methods described herein are a mixture of (R) and the (S) isomers. In one embodiment, the compounds useful in the methods described herein are pure (R)-isomers. In another embodiment, the compounds described herein are pure (S)-isomers.

As is known to an ordinarily skilled artisan, optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns) with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds can likewise be obtained by utilizing optically active starting materials in chiral synthesis processes under reaction conditions which do not cause racemization.

Where applicable, the present invention also relates methods involving administration of useful forms of the compounds as disclosed herein, such as free base forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, a maleate or a sodium salt.

In certain embodiments, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds described herein can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in crystal structure as crystalline structures of two different chemical compounds.

One of ordinary skill in the art will further recognize that some compounds described herein can exist in different solvate forms. Solvates of the compounds of the invention may form when solvent molecules are incorporated into the crystalline lattice structure of the compound molecule during the crystallization process. For example, a compound of as described in any embodiment herein may exist in the form of a hydrate, such as, for example, a monohydrate, hemihydrate, sesquihydrate, dihydrate, trihydrate, or any combination thereof.

The term "prodrug" means a compound that is a drug precursor which upon administration to a subject undergoes chemical conversion by metabolic or chemical processes to yield a compound of the present invention. Since prodrugs are known to enhance numerous desirable qualities of pharmaceuticals (e.g., solubility, bioavailability, manufacturing, etc.) the compounds of the present invention may be delivered in prodrug form. Thus, the present invention includes prodrugs of the disclosed compounds and methods of delivering the same. Prodrugs of a compound may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, isopropyl, butyl, isobutyl, sec-butyl, tert-butyl, cyclopropyl, phenyl, benzyl, and phenethyl esters, and the like. Such prodrugs are considered to be within the scope of this invention.

This invention provides, in other embodiments, for the metabolites of the compounds described herein. In one embodiment, the term "metabolite" refers to any substance produced from another substance by metabolism or a metabolic process.

Pharmaceutical Compositions

The compounds described herein can be administered alone or as an active ingredient of a formulation. Thus, the present invention also includes administration of pharmaceutical compositions or pharmaceutical product of compounds described herein, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form is closely related to the therapeutic amounts of the compounds or compositions which are desirable and efficacious for the given treatment application. Dosage forms include, but are not limited to, oral, rectal, sub-lingual, mucosal, nasal, ophthalmic, subcutaneous, intramuscular, topical, intravenous, transdermal, spinal, intrathecal, intra-articular, intra-arterial, sub-arachinoid, bronchial, lymphatic, and intra-uterile administration, and other dosage forms for systemic delivery of active ingredients.

To prepare pharmaceutical dosage forms, the active ingredient may be mixed with a pharmaceutical carrier according to conventional pharmaceutical compounding techniques. The carrier may take a wide variety of forms depending on the form of preparation desired for administration.

In one embodiment, the methods of this invention provide administering a pharmaceutical compositions containing the compounds of this invention and/or its analog, derivative, isomer, metabolite, pharmaceutically acceptable salt, pharmaceutical product, hydrate, N-oxide, or any combination thereof, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the compounds of this invention are formulated in a capsule. In one embodiment of the present invention, the compounds of this invention are formulated in a tablet. In accordance with this embodiment, the compositions of the present invention comprise, an inert carrier or diluent.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

In one embodiment, the mode of administration is topical. In additional embodiments, a compound described herein is applied as a cream. In additional embodiments a compound described herein is applied as a cream to the side of the eye lid of a subject in need thereof.

In certain embodiments, the pharmaceutical compositions are formulated as solutions, suspensions and other dosage forms suitable, in certain embodiments, for topical administration to the eye lid, margins of the eye, eye lashes and/or eye lid margin in order to deliver the formulation to the Meibomian gland orifice. In certain embodiments, liquid (aqueous or non-aqeuous) solutions are used, based on ease of formulation, as well as a patient's ability to easily administer such compositions by means of applying the formulation to the eye lid, eye lashes and/or eye lid margin. Application may be performed with an applicator, such as the patient's finger, a Weck-Cel®, Q-tip, or other device capable of delivering a formulation to the eye lid, eye lashes and/or eye lid margin in order to deliver the formulation to the Meibomian gland orifice. However, the compositions may also be, for example, creams, gel, ointments, suspensions, viscous or semi-viscous gels, or other types of solid or semi-solid compositions.

Any of a variety of carriers may be used in a formulation used in the present invention. In one embodiment, the carrier is a non-aqueous carrier (e.g., oil, or oil mixture) having a viscosity in a range which provides ocular surface protection via enhancement of the anti-evaporative lipid layer of the tear film (as evident by increased tear film break up time (TFBUT) and/or the ocular protection index (OPI)), acute protection of the Meibomian gland orifice, and increases the therapeutic efficacy of the active agent component by extending the residence time of the active agent to the Meibomian gland orifice, with minimal visual disruption (e.g., blurring), ocular irritation, or lid caking. For example, the viscosity of the non-aqueous carrier may range from about 50 cps to about 1000 cps, about 50 cps to about 500 cps, about 50 cps to about 200 cps, or about 60 cps to about 120 cps. In certain embodiments, the non-aqueous carrier comprises an oil, e.g., castor oil, olive oil, peanut oil, macadamia nut oil, walnut oil, almond oil, pumpkinseed oil, cottonseed oil, sesame oil, corn oil, soybean oil, avocado oil, palm oil, coconut oil, sunflower oil, safflower oil, flaxseed oil, grapeseed oil, canola oil, low viscosity silicone oil, light mineral oil, or any combination thereof.

In certain embodiments, a tear substitute may act as the pharmaceutical carrier. Suitable tear substitutes include, but are not limited to, monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; water soluble proteins such as gelatin; polymers, such as polyvinyl alcohol, polyvinylpyrrolidone, and povidone; carbomers, such as carbomer 934P, carbomer 941, carbomer 940 and carbomer 974P; and gums such as HP-guar. Many such tear substitutes are commercially available, which include, but are not limited to cellulose esters such as Bion Tears™, Celluvisco, Genteal™, OccuCoat 1™, Refresh™, Teargen II™, Tears Naturale™, Tears Naturale II™, Tears Naturale Free™, and TheraTears™; and polyvinyl alcohols such as Akwa Tears™, HypoTears™, Moisture Eyes™, Murine Lubricating™, Systane™ Lubricant Eye props, and Visine Tears™. Tear substitutes may also comprise paraffins, such as the commercially available Lacri-Lube™ ointments. Other commercially available ointments that may be used as tear substitutes include, for example, Lubrifresh PM™, Moisture Eyes PM™ and Refresh PMT™.

In certain embodiments, the tear substitute contains hydroxypropylmethylcellulose. In certain embodiments, the tear substitute is Genteal™ lubricating eye drops. GenTeal™ (CibaVision-Novartis) is a sterile lubricant eye drop containing hydroxypropyl methylcellulose 3 mg/g and preserved with sodium perborate.

In another embodiment, the tear substitute comprises carboxymethyl cellulose sodium. For example, without limitation, the tear substitute which comprises carboxymethyl cellulose sodium may be Refresh™ Tears. Refresh™ Tears is a lubricating formulation similar to normal tears, containing a mild non-sensitizing preservative, stabilised oxychloro complex (Purite™), that ultimately changes into components of natural tears when used.

Additional carriers may optionally be included in the formulations of the present invention. Examples of additional carriers include, for example, water, mixtures of water and water-miscible solvents, such as $C_{1-7}$-alkanols, vegetable oils, mineral oils or other oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, e.g., crosslinked polyacrylic acid, such as neutral Carbopol, or mixtures of those polymers. The concentration of the carrier may be, for example, from 1 to 100000 times the concentration of the active ingredient.

Additional ingredients that may be included in a formulation include, for example, tonicity enhancers, preservatives, solubilizers, non-toxic excipients, demulcents, sequestering agents, pH adjusting agents, co-solvents, viscosity building agents, and combinations thereof.

For the adjustment of the pH, for example to a physiological pH, buffers may be useful. In certain embodiments, the pH of a solution is maintained within the range of about 4.0 to about 8.0, such as, about 4.0 to about 6.0, for example, about 6.5 to about 7.8. Suitable buffers may be added, such as, e.g., boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Generally, buffers may be used in amounts ranging from about 0.05 to about 2.5 percent by weight, such as, from about 0.1 to about 1.5 percent by weight.

Tonicity may be adjusted, if needed, by the use of tonicity enhancing agents. Such agents may, for example, be of ionic and/or non-ionic type. Examples of ionic tonicity enhancers include, for example, alkali metal or earth metal halides, such as, for example, $CaCl_2$, KBr, KCl, LiCl, NaI, NaBr or NaCl, $Na_2SO_4$ or boric acid. Non-ionic tonicity enhancing agents include, for example, to urea, glycerol, sorbitol, mannitol, propylene glycol, or dextrose. An aqueous solution may be adjusted with a tonicity agent(s) to approximate the osmotic pressure of normal lacrimal fluids which is equivalent to a 0.9% solution of sodium chloride or a 2.5% solution of glycerol. In one embodiment, an osmolality of about 225 to about 400 mOsm/kg is obtained. In one embodiment, an osmolality of about 280 to about 320 mOsm is obtained.

In further embodiments, topical formulations may additionally comprise a preservative. A preservative may typically be selected from a quaternary ammonium compound such as benzalkonium chloride, benzoxonium chloride (e.g., N-benzyl-N—($C_8$-$C_{18}$ dimethylammonium chloride) or the like. Examples of preservatives different from quaternary ammonium salts include, for example, alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, Germal™ II or sorbic acid. In certain embodiments, preservatives are quaternary ammonium compounds, for example, benzalkonium chloride or its derivative such as Polyquad (see, e.g., U.S. Pat. No. 4,407,791), alkyl-mercury salts and parabens. Where appropriate, a sufficient amount of preservative may be added to the ophthalmic composition to ensure protection against secondary-contaminations during use caused by bacteria and fungi.

In another embodiment, topical formulations do not include a preservative. Such formulations may be useful for patients who wear contact lenses, or those who use several topical ophthalmic drops and/or those with an already compromised ocular surface, wherein limiting exposure to a preservative may be more desirable.

A topical formulation may additionally include a solubilizer, for example, if the active or the inactive ingredients tend to form a suspension or an emulsion. Suitable solubilizers include, but are not limited to, tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of those compounds. In certain embodiments, the solubilizer is a reaction product of castor oil and ethylene oxide, for example the commercial products Cremophor EL™ or Cremophor RH40™. Reaction products of castor oil and ethylene oxide have proved to be particularly good solubilizers that are tolerated extremely well by the eye. In another embodiment, the solubilizer is selected from tyloxapol and from a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

The formulations may further comprise non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight.

Other compounds may also be added to the formulations of the present invention to adjust (e.g., increase) the viscosity of the carrier. Examples of viscosity enhancing agents include, but are not limited to, polysaccharides, such as hyaluronic acid and its salts, chondroitin sulfate and its salts, dextrans, various polymers of the cellulose family; vinyl polymers; and acrylic acid polymers.

In embodiments wherein the formulation is an ointment, in certain embodiments, the ointment base used to prepare the ophthalmic ointment may be one that has been used in conventional ophthalmic ointments. For example, the base may be liquid paraffin, white petrolatum, purified lanolin, gelation hydrocarbon, polyethylene glycol, hydrophilic ointment base, white ointment base, absorptive ointment base, Macrogol (Trade Name) ointment base, simple ointment base, and the like.

An ophthalmic ointment may further comprise conventional excipients other than the ointment base. Examples of such excipients include, for example, antiseptics such as parahydroxybenzoate, chlorobutanol, benzalkonium chloride and the like; surfactants such as polysorbate 80, polyoxyl 40 stearate, polyoxyethylene hydrogenated castor oil and the like; stabilizers such as sodium edetate, citric acid, and salts thereof; alcohols such as glycerol, lanolin alcohol, cetanol and the like; esters such as isopropyl myristate, ethyl linoleate and the like; and oils such as olive oil and triglycerides of middle-chained fatty acids.

In additional embodiments, the composition may comprise pharmaceutically acceptable materials, compositions or vehicles, such as a liquid (aqueous or non-aqueous) or solid filler, diluent, excipient, solvent or encapsulating material, involved in carrying or transporting or delivering an agent to the surface of the eye. Each carrier must be "acceptable" in the sense of being compatible with the other ingredients of the composition and not injurious to the patient. Some additional examples of materials which may serve as pharmaceutically acceptable carriers include, for example, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils such as castor oil, olive oil, peanut oil, macadamia nut oil, walnut oil, almond oil, pumpkinseed oil, cottonseed oil, sesame oil, corn oil, soybean oil, avocado oil, palm oil, coconut oil, sunflower oil, safflower oil, flaxseed oil, grapeseed oil, canola oil, low viscosity silicone oil, light mineral oil, or any combination thereof, (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) gums such as HP-guar; (22) polymers; and (23) other non-toxic compatible substances employed in pharmaceutical formulations.

The preparation of pharmaceutical compositions which contain an active component is well understood in the art. The active therapeutic ingredient is often mixed with excipients which are pharmaceutically acceptable and compatible with the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, citric and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compounds of this invention are pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, lactic acid, acetic acid, formic acid, methanesulphonic acid, fumaric acid, maleic acid, succinic acid, acetic acid, benzoic acid, oxalic acid, citric acid, tartaric acid, carbonic acid or phosphoric acid.

In some embodiments, the compounds of the present invention are administered as a mono-therapy. In other embodiments, the compounds of the present invention are administered as part of a combination therapy. For example, compounds described herein may be used in combination with other drugs or therapies that are used in the treatment of the diseases or conditions for which compounds described herein are useful. In such combinations, each active ingredient can be administered either in accordance with their usual dosage range or a dose below their usual dosage range. For example, a compound described herein may be adjunctively administered in combination with anti-infectives (e.g., tetracycline antibiotics), vasoconstrictors, antiallergenic agents, anesthetics, analgesics, dry eye agents (e.g. secretagogues, mucomimetics, polymers, lipids, antioxidants), etc, or any combination thereof.

Such other drug(s) may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein may be employed. Accordingly, the pharmaceutical compositions of the present invention include those that also contain one or more other active ingredients, in addition to a compound described herein.

By adjunctive administration it is meant simultaneous administration of the compounds in the same-dosage form, simultaneous administration in separate dosage forms, and separate administration of the compounds.

In one embodiment, the methods of this invention comprise administration of a compound of this invention at various dosages. In one embodiment, the compound of this invention is administered at a dosage of about 0.01 to about 200 mg per day. In one embodiment, the compound of this invention is administered at a dose of about 0.1 to about 150 mg, or in another embodiment, 0.1 to about 100 mg, or in another embodiment, about 0.1 to about 75 mg, or in another embodiment, about 0.1 to about 50 mg, or in another embodiment, about 0.5 to about 100 mg, or in another embodiment, about 0.5 to about 75 mg, or in another embodiment, about 0.5 to about 50 mg, or in another embodiment, about 0.5 to about 25 mg, or in another embodiment, about 1 to about 100 mg, or in another embodiment, 1 about 1 to about 75 mg, or in another embodiment, about 1 to about 50 mg, or in another embodiment, about 1 to about 25 mg.

In one embodiment, the methods of this invention comprise administration of a compound of this invention at various dosages. In one embodiment, a compound of this invention is administered at a dosage of about 0.01 mg. In another embodiment a compound of this invention is administered at a dosage of about 0.1 mg, about 0.25 mg, about 0.5 mg, about 0.75 mg, about 1 mg, about 1.25 mg, about 1.5 mg, about 1.75 mg, about 2 mg, about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg or about 100 mg.

In further embodiments, the methods of this invention comprise administration of a compound of this invention at a dosage of about 0.01 mg/kg to about 5 mg/kg, for example, about 0.1 mg/kg to about 3 mg/kg. In other embodiments a compound of this invention is administered at a dosage of about 0.1 mg/kg, about 0.25 mg/kg, about 0.5 m/kg, about 0.625 mg/kg, about 0.75 mg/kg, about 1 mg/kg, about 1.25 mg/kg, about 1.5 mg/kg, about 1.75 mg/kg, about 2 mg/kg, about 2.5 mg/kg, about 3 mg/kg, about 3.5 mg/kg, about 4.5 mg/kg or about 5 mg/kg.

The term "treating" means to relieve, alleviate, delay, reduce, reverse, improve or prevent at least one symptom of a condition in a subject. The term "treating" refers to relieving, alleviating, delaying, reducing, reversing, improving or preventing at least one symptom selected from abnormal Meibomian gland secretions, Meibomian gland dysfunction, dry eye, Meibomian gland secretions, redness of the eyelid margins, burning and/or itching in a subject's eye, ocular discomfort, corneal epithelial erosion, ocular and conjunctival staining, and reducing blurred and/or fuzzy vision. The term "treating" may also mean to arrest, delay the onset (i.e., the period prior to clinical manifestation of a disease) and/or reduce the risk of developing or worsening a condition. The compounds of the present invention may be administered as a mono-therapy or administered as part of a combination therapy. For example, one or more of the compounds of the present invention may be co-administered or used in combination with one or more additional therapies known in the art.

An "effective amount" means the amount of a compound described herein that, when administered to a patient (e.g., a mammal) for treating a disease, is sufficient to effect such treatment for the disease, or an amount of a compound described herein that is sufficient to achieve an objective of the invention (e.g., treating a Meibomian gland dysfunction). The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects (see, e.g., Ofri R, et al. *The Veterinary Journal*, 174, 536-540, 2007), farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The term "palmitate:stearate ratio" may be used herein as a marker ratio reflecting the underlying fatty acid composition in the lipids of tears.

The term "abnormal Meibomian gland secretion" refers to a Meibomian gland secretion with, for example, increased viscosity, increased melting point, decreased palmitate to stearate ratio, increased opacity or increased color and/or an increased time (refractory period) between gland secretions, decreased TFBUT, etc.

The term "normalizing a Meibomian gland dysfunction" refers to, for example, decreasing the viscocity, decreasing the melting point, increasing the palmitate to stearate ratio, decreasing the opacity or decreasing the color of a Meibomian gland secretion and/or decreasing the time (refractory period) between gland secretions, increased TFBUT, etc.

The term "blepharitis" refers to a disorder comprising inflammation of the lid margin in which abnormal Meibomian gland secretions play a role and lid keratinization, lid margin rounding, obscuration of the grey line, increased lid margin transparency, and increased vascularity are observed. Although the terms Meibomian gland dysfunction and Meibomianitis are commonly referred to as blepharitis by most investigators, it is important to note that these are distinct diseases associated with abnormal Meibomian gland secretions and that the terms are not interchangeable.

It is to be understood that any use of any of the compounds as herein described may be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

EXAMPLES

Example 1

Synthesis of (S)—N-(4-Cyano-3-(trifluoromethyl)phenyl)-3-(4-cyanophenoxy)-2-hydroxy-2-methyl-propanamide (Compound 1)

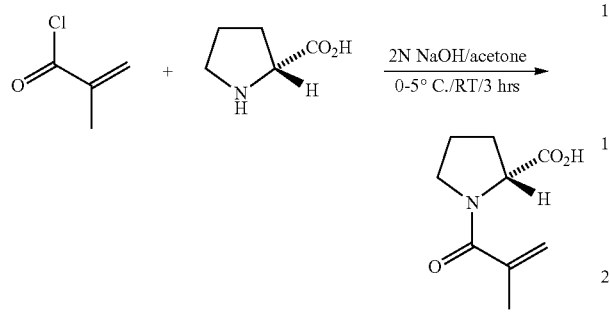

(2R)-1-Methacryloylpyrrolidin-2-carboxylic Acid.

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 g (68%) of the desired compound as colorless crystals: mp 102-103° C.; the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C═O), 1647 (CO, COOH), 1584, 1508, 1459, 1369, 1348, 1178 cm$^{-1}$.

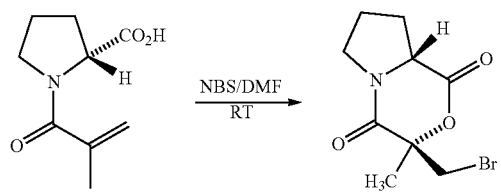

(3R,8aR)-3-Bromomethyl-3-methyl-tetrahydro-pyrrolo[2,1-c][1,4]oxazine-1,4-dione.

A solution of NBS (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C═O), 1687 (C═O), 1448, 1377, 1360, 1308, 1227, 1159, 1062 cm$^{-1}$; $[\alpha]_D^{26}$+124.5° (c=1.3, chloroform).

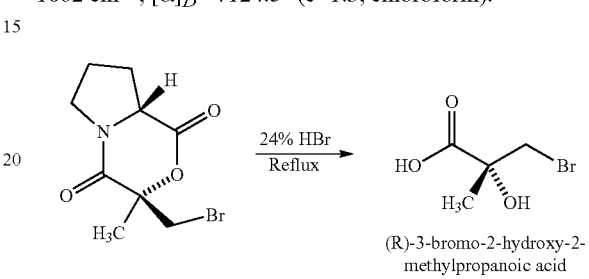

(2R)-3-Bromo-2-hydroxy-2-methylpropanoic Acid.

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C═O), 1449, 1421, 1380, 1292, 1193, 1085 cm$^{-1}$; $[\alpha]_D^{26}$+10.5° (c=2.6, MeOH).

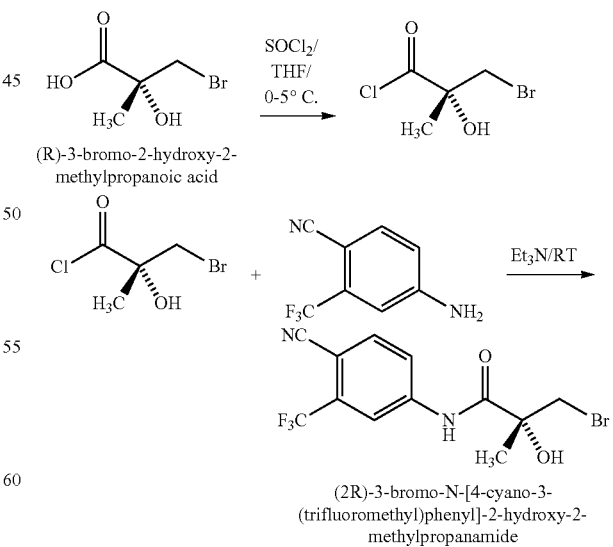

(2R)-3-Bromo-N-[4-cyano-3-(trifluoromethyl)phenyl]-2-hydroxy-2-methylpropanamide.

Thionyl chloride (46.02 g, 0.39 mol) was added dropwise to a cooled solution (less than 4° C.) of (2R)-3-bromo-2- hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid. $^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.

The filtrate was concentrated under reduced pressure to give an oil. This oil was purified by column chromatography using CH$_2$Cl$_2$/EtOAc (80:20) to give an oil which was crystallized from CH$_2$Cl$_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type). $^1$H NMR (CDCl$_3$/TMS) δ 1.63 (s, 3H, CH$_3$), 3.35 (s, 1H$_2$OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M-H]$^-$ 388.1. Mp: 92-94° C.

Example 2

Synthesis of (S)—N-(4-cyano-3-(trifluoromethyl)phenyl)-3-(4-cyano-3-fluorophenoxy)-2-hydroxy-2-methylpropanamide (Compound 2)

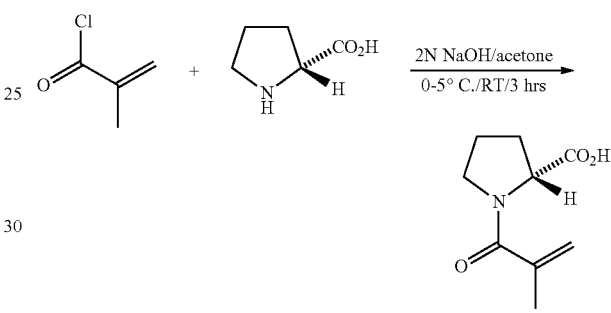

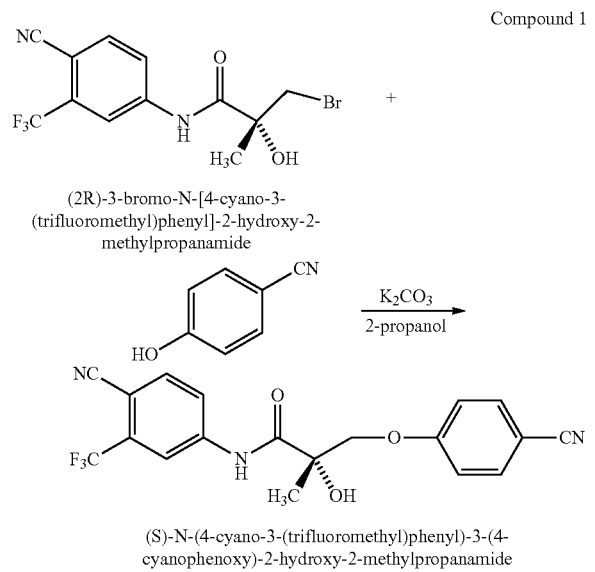

(S)—N-(4-Cyano-3-(trifluoromethyl)phenyl)-3-(4-cyanophenoxy)-2-hydroxy-2-methylpropanamide (Compound 1).

A mixture of bromoamide ((2R)-3-bromo-N-[4-cyano-3-(trifluoromethyl)phenyl]-2-hydroxy-2-methylpropanamide, 50 g, 0.14 mol), anhydrous K$_2$CO$_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H$_2$O and then extracted with EtOAc (2×300 mL). The combined EtOAc extracts were washed with 10% NaOH (4×200 mL) and brine. The organic layer was dried over MgSO$_4$ and then concentrated under reduced pressure to give an oil which was treated with 300 mL of ethanol and an activated carbon. The reaction mixture was heated to reflux for 1 h and then the hot mixture was filtered through Celite.

(2R)-1-Methacryloylpyrrolidin-2-carboxylic Acid.

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite, and evaporated in vacuo to give the crude product as a colorless oil. Recrystallization of the oil from ethyl ether and hexanes afforded 16.2 g (68%) of the desired compound as colorless crystals: mp 102-103° C.; the NMR spectrum of this compound demonstrated the existence of two rotamers of the title compound. $^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (m) for the second rotamer (totally 1H for both rotamers, CH at the chiral center), 3.57-3.38 (m, 2H, CH$_2$), 2.27-2.12 (1H, CH), 1.97-1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737

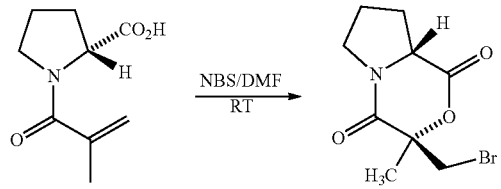

(3R,8aR)-3-Bromomethyl-3-methyl-tetrahydro-pyrrolo[2,1-c][1,4]oxazine-1,4-dione.

A solution of NBS (23.5 g, 0.132 mol) in 100 mL of DMF was added dropwise to a stirred solution of the (methacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C.; $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform).

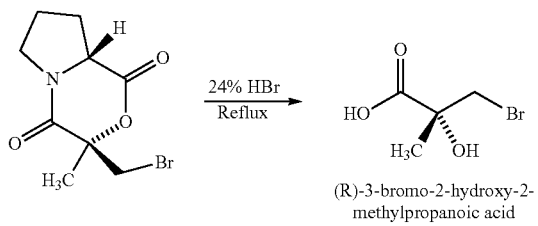

(2R)-3-Bromo-2-hydroxy-2-methylpropanoic Acid.

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C.; $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$+10.5°(c=2.6, MeOH).

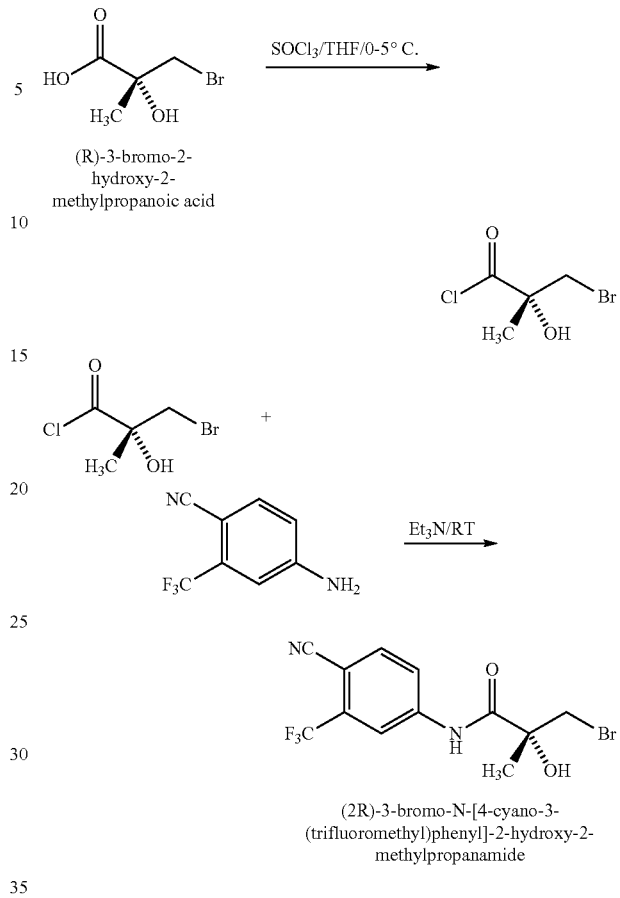

Synthesis of (2R)-3-Bromo-N-[4-cyano-3-(trifluoromethyl)phenyl]-2-hydroxy-2-methylpropanamide.

Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid. $^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.

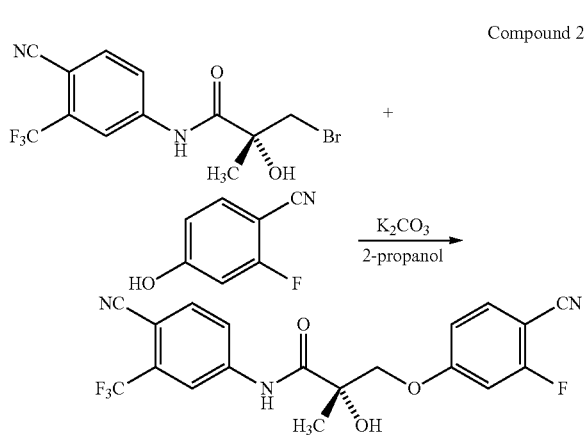

Compound 2

Synthesis of (S)—N-(4-cyano-3-(trifluoromethyl)phenyl)-3-(4-cyano-3-fluorophenoxy)-2-hydroxy-2-methylpropanamide (Compound 2).

A mixture of bromoamide ((2R)-3-bromo-N-[4-cyano-3-(trifluoromethyl)phenyl]-2-hydroxy-2-methylpropanamide (2.0 g, 5.70 mmol), anhydrous $K_2CO_3$ (2.4 g, 17.1 mmol) in 50 mL of acetone was heated to reflux for 2 h and then concentrated under reduced pressure to give a solid. The resulting solid was treated with 2-fluoro-4-hydroxybenzonitrile (1.2 g, 8.5 mmol) and anhydrous $K_2CO_3$ (1.6 g, 11.4 mmol) in 50 mL of 2-propanol, was heated to reflux for 3 h, and then concentrated under reduced pressure to give a solid. The residue was treated with 100 mL of $H_2O$ and then extracted with EtOAc (2×100 mL). The combined EtOAc extracts were washed with 10% NaOH (4×100 mL) and brine, successively. The organic layer was dried over $MgSO_4$ and then concentrated under reduced pressure to give an oil which was crystallized from $CH_2Cl_2$/hexane to give 0.5 g (23%) of (S)—N-(4-cyano-3-(trifluoromethyl)phenyl)-3-(4-cyano-3-fluorophenoxy)-2-hydroxy-2-methylpropanamide as a colorless solid. $^1$H NMR ($CDCl_3$/TMS) δ 1.63 (s, 3H, $CH_3$), 3.34 (bs, $1H_2OH$), 4.08 (d, J=9.17 Hz, 1H, CH), 4.50 (d, J=9.17 Hz, 1H, CH), 6.74-6.82 (m, 2H, ArH), 7.50-7.55 (m, 1H, ArH), 7.81 (d, J=8.50 Hz, 1H, ArH), 7.97 (q, J=2.03, 8.50 Hz, 1H, ArH), 8.11 (d, J=2.03 Hz, 1H, ArH), 9.12 (s, 1H, NH). Calculated Mass: 407.1, [M+Na]$^+$430.0. Mp: 124-125° C.

Example 2A

Synthesis of (S)—N-(4-cyano-3-(trifluoromethyl)phenyl)-3-(4-fluorophenoxy)-2-hydroxy-2-methylpropanamide (Compound 3)

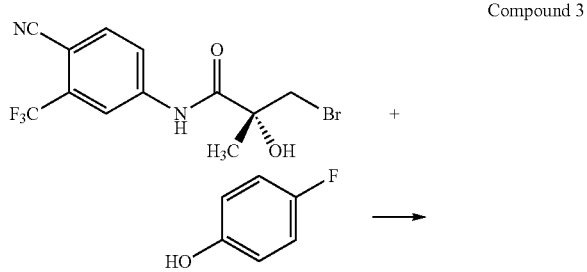

Compound 3

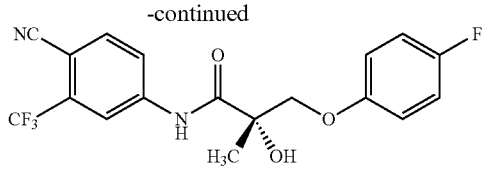

A mixture of bromoamide ((2R)-3-bromo-N-[4-cyano-3-(trifluoromethyl)phenyl]-2-hydroxy-2-methylpropanamide (44.0 g, 125 mmol), anhydrous $K_2CO_3$ (51.9 g, 376 mmol) in 800 mL of acetone was heated to reflux for 2 h, which monitored by TLC indicated complete conversion to the epoxy intermediates. After cooling to room temperature, the solution was filtered through the Celite 545 pad to remove insoluble solid. The solution was concentrated under reduced pressure. To the flask was added additional anhydrous $K_2CO_3$ (34.6 g, 250 mmol) and 4-fluorophenol (14.05 g, 125 mmol) in 800 mL of methylethylketone and heated to reflux overnight. Then, the solution was through Celite 545 pad and concentrated under reduced pressure, diluted to extra EtOAc, washed with water, saturated $NaHCO_3$, water, dried by anhydrous $MgSO_4$, concentrated and purified by column chromatography (EtOAc/Hexane) or recrystallization with methylene chloride to give the desired compound 3 (36.77 g, 76.9%) as a white solid. $^1$H NMR ($CDCl_3$, 300 MHz) δ 1.59 (s, 3H, $CH_3$), 3.39 (bs, $1H_2OH$), 3.95 (d, J=9.2 Hz, 1H, CH), 4.43 (d, J=9.2 Hz, 1H, CH), 6.85 (m, 2H, ArH), 6.98 (m, 2H, ArH), 7.80 (d, J=8.4 Hz, 1H, ArH), 7.96 (dd, J=8.4, 1.8 Hz, 1H, ArH), 8.08 (d, J=1.8 Hz, 1H, ArH), 9.13 (bs, 1H, NH). Calculated Mass: 382.1, [M-H]$^-$ 380.9. Mp: 143-144° C.

Example 3

Tear Composition Following Treatment with Compound 2

The goal of this study was to compare the effect of Compound 2 to testosterone propionate (TP) on tear composition in an acute, orchiectomized (ORX) rabbit model.

Materials and Methods

Fifteen New Zealand white rabbits weighing approximately 3 lbs were allowed to acclimate for 4 weeks before the start of the study. Animals were weighed on day 0 of the study, randomized according to body weight and allotted to the following dose groups:
1) Intact, Topical Vehicle (n=3)
2) ORX, Topical Vehicle (n=3)
3) ORX, Topical Compound 2, 2.5 mg/kg (n=3)
4) ORX, Subcutaneous Compound 2, 2.5 mg/kg (n=3)
5) ORX, Subcutaneous Testosterone Propionate (TP), 2.5 mg/kg (n=3)

Pre-dose tear and blood samples were collected. Animals from groups 2-5 were to premedicated with glycopyrrolate (0.02 mg/kg) and then anesthesia was induced with a combination of ketamine (15 mg/kg): medetomidine (0.25 mg/kg).

Anesthesia was maintained with isoflurane (1 liter/hr). Orchiectomy was performed using a scrotal incision. Animals were revived from anesthesia using atipamezole (1 mg/kg) SQ. Analgesia was provided with buprenorphine (0.05 mg/kg) Immediately after the animals had recovered from anesthesia, they received their first dose with the appropriate test articles as indicated above.

Drug dosing was done once daily for 14 days. Blood was collected at 60 minutes post administration of the last dose of drug and plasma separated for HPLC analysis of parent drug concentrations.

Tears were collected using Schirmer tear strips (Alcon, Tex.) on day 0 before surgery, 24 hours after the last administration of drug (day 15) and also at 42 days (6 weeks after start of study). The tears were stored at −80° C. prior to lipid analysis.

Lipids were hydrolyzed, extracted from the Schirmer strips, derivatized, and subjected to gas chromatography with flame ionization detector (GCFID) to evaluate the lipid composition.

The samples were evaluated for the presence of 28 saturated and unsaturated fatty acids that included methyl caprate (C10:0), methyl laurate (C12:0), methyl 11-dodecenoate (C12:1), methyl myristate (C14:0), methyl myristoleate (C14:1), methyl palmitate (C16:0), methyl palmitoleate (C16:1), methyl stearate (C18:0), methyl oleate (C18:1), methyl vaccenate (C18:1), methyl linoleate (C18:2), methyl gamma linoleate (C18:3), methyl linoleate (C18:3), methyl arachidate (C20:0), methyl 11-eicosenoate (C20:1), methyl 11,14 eicosadinoate (C20:2), methyl 8,11,14 eicosatrienoate (C20:3), methyl eicosapentaenoate (C20:5), methyl behenate (C22:0), methyl erucate (C22:1), methyl 13,16 docosaenoate (C22:2), methyl docosatetraenoate (C22:4), methyl docosapentaenoate (C22:5), methyl docosahexaenoate (C22:6), methyl lignocerate (C24:0), and methyl nervonate (C24:1).

The area under the curve for each individual peak was determined using GC ChemStation software. During the extraction process, seven samples showed an emulsion between aqueous and solvent phases and did not dry well. These samples were then washed with a saturated solution of NaCl+0.1% formic acid (FA). Four samples did not show any peaks on GC-FID and were excluded from analysis. These samples were all in the predose tear group. Two more samples from the predose group and one sample from Vehicle Intact treated group had small but clear and well to separated peaks that were included in the analysis.

To normalize for the tear content, the lipid composition was expressed as a ratio of the lipid that was most affected by castration (palmitate) to one which remained relatively constant (stearate). Blood was also collected on day 15 (24 hours after last drug administration) of the study, plasma separated and analyzed for Compound 2.

Table 1 shows the statistical analysis of tear fatty acid composition. As can be seen from Table 1, analysis of the pre-dose tear samples showed that the palmitate:stearate ratio was 1.71±0.52. Following administration of topical vehicle the palmitate:stearate ratio increased to 2.6±0.28 in the Intact vehicle treated group and 2.16±0.85 in the ORX vehicle treated group. Upon treatment with TP, there was a significant increase in the palmitate:stearate ratio to 4.18±0.51. A similar increase in fatty acid ratio (3.96±0.46) was seen with topical administration of Compound 2, while subcutaneous administration of Compound 2 gave a moderate increase in fatty ratio of 3.12±0.99. Also see FIG. 1.

TABLE 1

| Gonadal Status | Treatment | Dose | | Palmitate:stearate ratio |
|---|---|---|---|---|
| Intact | Predose | 0 | Mean | 1.71 |
|  |  |  | S.D. | 0.522 |
| ORX | ORX Topical Vehicle | 0 | Mean | 2.16 |
|  |  |  | S.D. | 0.853 |
| ORX | ORX Topical Compound 2 | 2.5 mg/kg | Mean | 3.96[a,b] |
|  |  |  | S.D. | 0.459 |
| Intact | Intact Topical Vehicle | 0 | Mean | 2.60[a] |
|  |  |  | S.D. | 0.283 |

TABLE 1-continued

| Gonadal Status | Treatment | Dose | | Palmitate:stearate ratio |
|---|---|---|---|---|
| ORX | ORX SQ Compound 2 | 2.5 mg/kg | Mean | 3.12[a] |
|  |  |  | S.D. | 0.99 |
| ORX | ORX SQ TP | 2.5 mg/kg | Mean | 4.18[a,b] |
|  |  |  | S.D. | 0.505 |

[a]$P < 0.05$ when compared to ORX Vehicle controls
[b]$P < 0.05$ when compared to Intact vehicle controls Systemic exposures after topical and subcutaneous administration were determined in peripheral blood samples collected one hour after drug administration on the last day of the study. Plasma concentrations of Compound 2 were measured using LCMS. See Table 2. Mean plasma concentrations of Compound 2 following topical administration were 1177±398.72 nM, while mean levels were 1210±311.93 nM in animals that received subcutaneous (SQ) doses. These data to indicate that significant systemic absorption of Compound 2 occurred after topical administration in this vehicle.

TABLE 2

| Compound | mean (nM) | SD |
|---|---|---|
| Vehicle | 0 | 0 |
| Compound 2: Topical | 1177 | 398.7192 |
| Compound 2: Subcutaneous | 1210 | 311.9295 |

Figure 2:
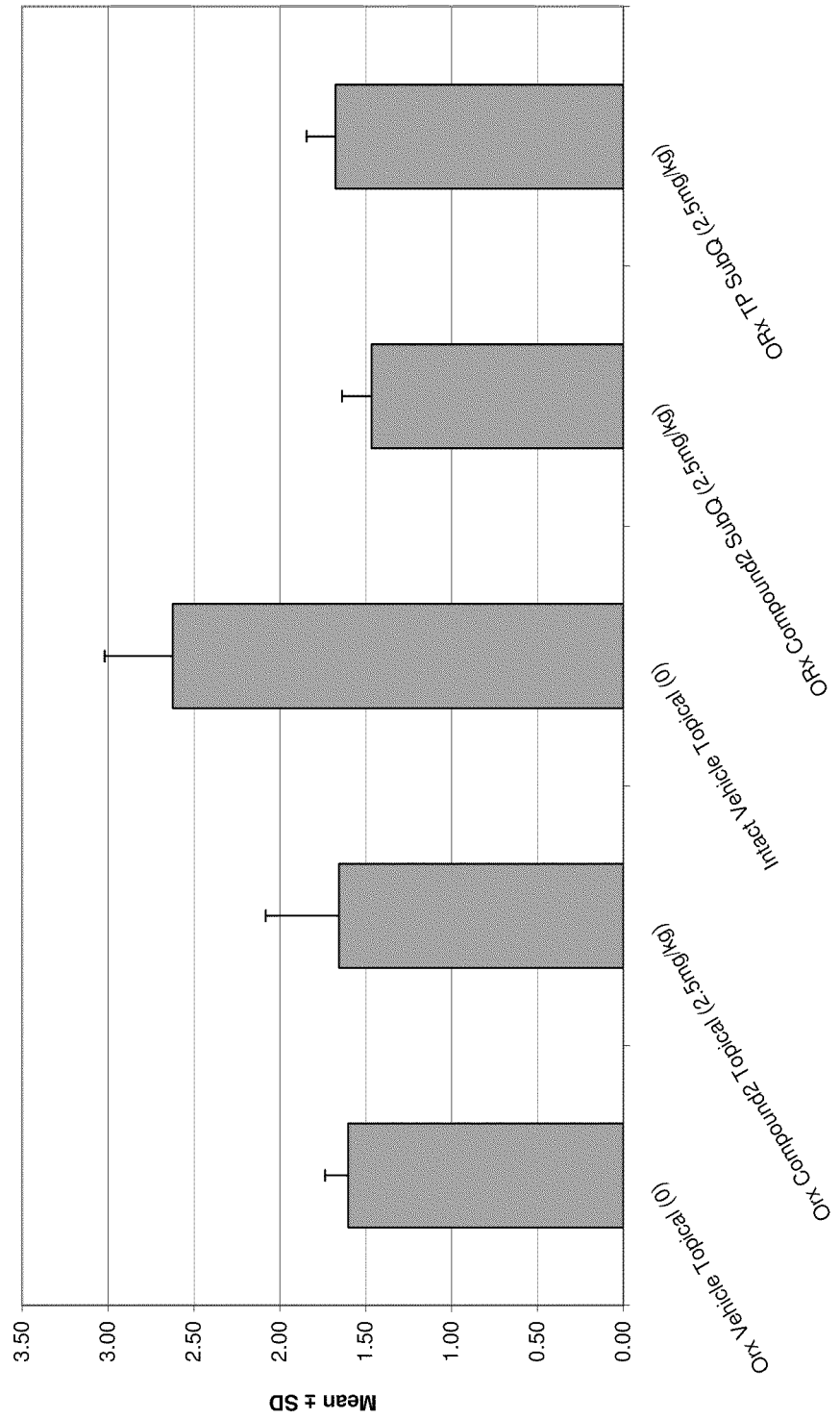
FIG. 2 depicts the tear fatty acid composition following the 4 week washout period as described in Example 3 (a: p<0.05 compared to castrated vehicle treated animals; b: p<0.05 compared to intact vehicle treated animals).

The last dose of drug or vehicle was administered on day 15 of the study Animals were left untreated for 4 weeks (washout period) before tear samples were collected again on Schirmer tear strips and analyzed as indicated above. Analysis of the tears from these animals showed that ORX vehicle treated animals had a significant reduction in the tear palmitate:stearate ratios (1.6±0.135) compared to animals in the Intact vehicle group (2.62±0.395) (FIG. 2) Animals that were treated for two weeks with Compound 2 (topical or SQ) or TP and then left untreated for 4 weeks showed a significant drop in the tear palmitate:stearate levels, with values similar to that of the ORX vehicle group (1.66±0.426, 1.47±0.172 and 1.67±0.17, respectively) (FIG. 2). These data show that TP and Compound 2 are essential for maintaining the saturated fatty acid profile of tears.

In this study, the composition of fatty acids from tears in the rabbits instead of from extracts of Meibomian glands was evaluated. The data given above indicates that castration decreases the levels of the saturated fatty acid palmitate in the tears of the rabbits (as measured by palmitate:stearate ratio). Also, the study shows that treatment with TP or Compound 2 significantly increases the palmitate:stearate ratio in the tears to two times that of intact animals, showing that this fatty acid is very sensitive to androgenic stimulation. Topical administration of Compound 2 increased palmitate:stearate ratios much more than systemic administration, most likely due to the ready availability of the drug to the Meibomian glands following administration to the eyelids. Vehicle treatment also caused a modest but lesser increase in the palmitate:stearate ratio indicating a placebo effect.

Example 4

The goal of this study was to compare the effects of Compound 1 and Compound 2, two tissue selective SARMs with differing androgenic potential, in modulating tear composition in an acute orchiectomized (ORX) rabbit model.

Materials and Methods

Twenty New Zealand white rabbits weighing approximately 3 lbs were allowed to acclimate for two weeks before the start of the study Animals were weighed on day 0 of the study, randomized according to body weight and allotted to the following dose groups:

1) Intact, sham operated, Topical Vehicle (n=5)
2) ORX, Topical Vehicle, (n=5)
3) ORX, Topical Compound 2, 2.5 mg/kg (n=5)
4) ORX, Topical Compound 1, 2.5 mg/kg (n=5)

Surgery

Surgeries for the study were staggered to limit the maximum number of surgeries per day to six. One animal from each group was entered into the study every day and either sham or orchiectomy was performed as described below Animals were premedicated with glycopyrrolate (0.02 mg/kg) and anesthesia was induced with a combination of ketamine (15 mg/kg): medetomidine (0.25 mg/kg). Anesthesia was maintained with isoflurane (1 liter/hr). ORX was performed using a scrotal incision. For the sham operated animals, the scrotal sac was incised and skin closed using tissue glue Animals were revived from anesthesia using atipamezole (1 mg/kg) SQ. Analgesia was provided with buprenorphine (0.05 mg/kg).

Dosing and Sample Collection

Immediately after the animals had recovered from anesthesia, they were dosed with the appropriate test articles as indicated above. Drug dosing was done once daily for 14 d. Blood samples were collected at 30, 60, 120, 240 and 1440 minutes after dose administration on day 11 for pharmacokinetic analyses. Plasma was separated for HPLC analysis of parent drug concentrations. Tears were collected using Schirmer tear strips (Alcon, Tex.) on day 0 before surgery and 24 hours after the last administration of drug (day 15). The tears were stored at −80° C. until shipment for analysis. Lipids were hydrolyzed, extracted from the Schirmer strips, derivatized, and subjected to GC-FID to evaluate the lipid composition. The samples were evaluated for the presence of 28 saturated and unsaturated fatty acids that included methyl caprate (C10:0), methyl laurate (C12:0), methyl 11-dodecenoate (C12:1), methyl myristate (C14:0), methyl myristoleate (C14:1), methyl palmitate (C16:0), methyl palmitoleate (C16:1), methyl stearate (C18:0), methyl oleate (C18:1), methyl vaccenate (C18:1), methyl linoleate (C18:2), methyl gamma linoleate (C18:3), methyl linoleate (C18:3), methyl arachidate (C20:0), methyl 11-eicosenoate (C20:1), methyl 11,14 eicosadinoate (C20:2), methyl 8,11,14 eicosatrienoate (C20:3), methyl eicosapentaenoate (C20:5), methyl behenate (C22:0), methyl erucate (C22:1), methyl 13,16 docosaenoate (C22:2), methyl docosatetraenoate (C22:4), methyl docosapentaenoate (C22:5), methyl docosahexaenoate (C22:6), methyl lignocerate (C24:0), and methyl nervonate (C24:1). Area under the curve for each individual peak was determined using the GC ChemStation software. To normalize for the tear content, the lipid composition was expressed as a ratio of the lipid that was most affected by castration (palmitate) to one which remained relatively constant (stearate).

At the end of the study, the animals were euthanatized. The left harderian and Meibomian glands were collected for lipid analysis and snap frozen using an ethanol:dry ice bath. Samples were stored at −80° C. until shipment for analysis. The right eyelids were embedded in OCT medium and shipped to Paragon Biosciences (Washington D.C.) for histology and Oil-red-O quantification of lipids. Images of three separate fields were taken from each eyelid at random and the amount of cells staining red in each field was scored using commercially available software. A scoring scheme was adopted with a scale of 0-4 to evaluate the staining intensities with 0=<1% cells stained, 1+ for 2-5% of cells stained, 2+=6-10% stain, 3+=11-20% staining, 4+ for >21% cells stained.

Pharmacokinetic Data Analysis

Plasma samples collected after dosing on day 11 were analyzed using an LCMS/MS method. Briefly, plasma samples were prepared by protein precipitation extraction. (S)—N-(4-Cyano-3-(trifluoromethyl)phenyl)-3-(4-chlorophenoxy)-2-hydroxy-2-methylpropanamide was used as internal standard for plasma samples. The analysis of Compound 1 and Compound 2 was performed using LC-MS/MS system consisting of an Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard column (SecurityGuard™ 4.0×2.0 mm ID, Phenomenex).

Mobile phase consisted of 60% acetonitrile, 40% water and 0.1% formic acid. Mobile phase was delivered at a flow rate of 0.3 mL/min. Multiple reaction monitoring (MRM) scans were made in curtain gas at a source temperature of 500° C. Molecular ions were formed using an ion spray voltage of −4500 V. Product ions formed in nitrogen gas at a declustering potential of −55 V (Compound 1), −64 V (Compound 2), and −78 V (Internal standard) and collision energy of −24.0 V (Compound 1, m/z 388.0→117.9), −26.0 V (Compound 2, m/z 406.1→135.9), and −22.4 V (Internal standard, m/z 396.9→241.0). The plasma concentration—time data were analyzed by non-compartmental methods using WinNonlin (Version 3.1, Pharsight Corporation, Mountain View, Calif., USA). The area under the plasma concentration—time curve from time zero to infinity (AUC) was calculated by the trapezoidal rule with extrapolation to time infinity. Table 3 shows the statistical analysis of the tear fatty acid composition.

TABLE 3

| Gonadal Status | Compound | Dose | | Palmitate:Stearate Ratios in tears | Palmitate:stearate ratios in Meibomian glands | Palmitate:stearate ratios in harderian glands |
|---|---|---|---|---|---|---|
| Intact | Pre-dose | 0 | Mean | 2.14 | n/a | n/a |
|  |  |  | S.D. | 0.526 |  |  |
| Intact | Vehicle | 0 | Mean | 3.33[a,b] | 2.72 | 5.18 |
|  |  |  | S.D. | 0.812 | 0.437 | 2.38 |
| ORX | Vehicle | 0 | Mean | 1.94[a] | 2.46 | 5.16 |
|  |  |  | S.D. | 0.193 | 0.635 | 4.29 |
| ORX | Compound 1 | 2.5 mg/kg | Mean | 2.97[a,b] | 4.07[b] | 5.1 |
|  |  |  | S.D. | 0.678 | 1.35 | 1.44 |
| ORX | Compound 2 | 2.5 mg/kg | Mean | 5.31[a,b] | 2.82 | 7.76 |
|  |  |  | S.D. | 1.56 | 1.15 | 3.01 |

Figure 3:
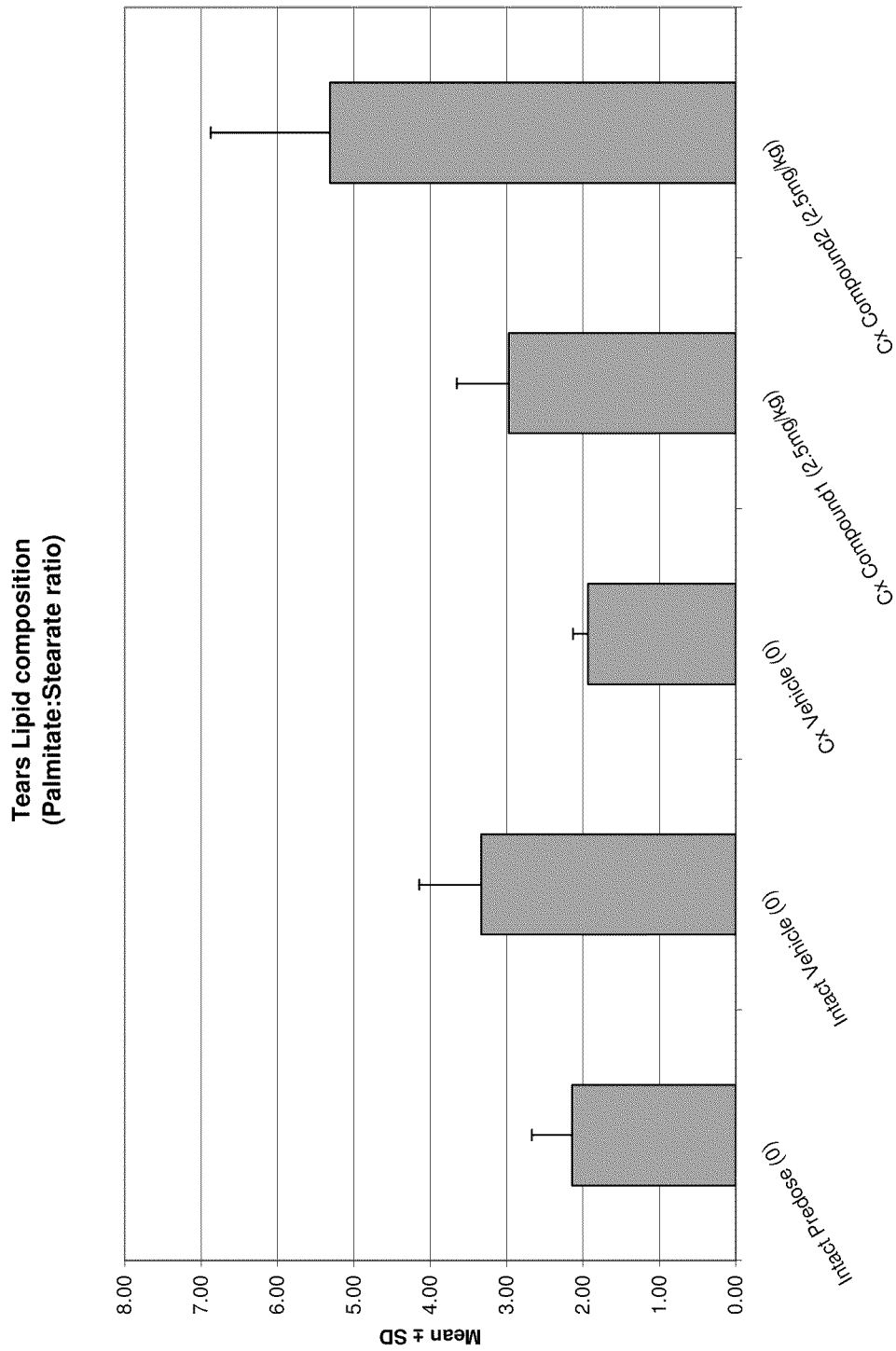
FIG. 3 depicts the tear fatty acid composition in response to the drug treatment described in Example 4 (a: p<0.05 compared to pre-dose intact lebels; b: p<0.05 compared to ORX vehicle treated animals).

[a]$P < 0.05$ when compared to pre-dose intact levels
[b]$P < 0.05$ when compared to ORX vehicle treated controls Analysis of the pre-dose tear samples showed that the palmitate:stearate ratio was 2.14±0.526. As can be seen from Table 3, following administration of topical vehicle, the palmitate:stearate ratio increased to 3.3±0.812 in the intact vehicle treated group and 1.94±0.193 in the ORX vehicle treated group (Table 3). Upon treatment with Compound 2, there was a significant increase in the palmitate:stearate ratio to 5.31±1.56. A similar increase in fatty acid ratio (2.97±0.678) was seen with topical administration of Compound 1. The fatty acid changes seen with Compounds 1 and 2 were statistically significant compared to ORX vehicle treated animals and pre-dose intact animals (FIG. 3 and Table 3).

Lipid analysis of the harderian glands showed a high degree of variability between animals In the harderian glands, Compound 2 showed a significant increase in palmitate:stearate ratios compared to that observed in the control animals. However, no change was seen with Compound 1 (Table 3). Lipid levels in the Meibomian glands showed a two fold increase of palmitate:stearate ratio with Compound 1. Treatment with Compound 2 showed a mild increase (Table 3).

Oil-Red-O is a lipophilic dye that is commonly used to stain lipid containing cells in histological sections. The amount of Oil-Red-O stain in each section is proportional to the number of cells synthesizing or storing lipid. A relative scoring system was adopted to evaluate the differences in lipid content of the Meibomian gland sections from treated and untreated animals in the study. Sham operated animals had an Oil-Red-O score of 3.75, while the ORX vehicle-treated animals showed a moderate decrease of approximately 15% (score=3.2). Upon treatment with Compound 2, the lipid staining was seen to increase to that of the intact animals (score=3.8). Compound 1 treated animals showed a mild increase over (score=3.4) that of the ORX animals.

Pharmacokinetic Analysis of Rabbit Plasma

Figure 4:
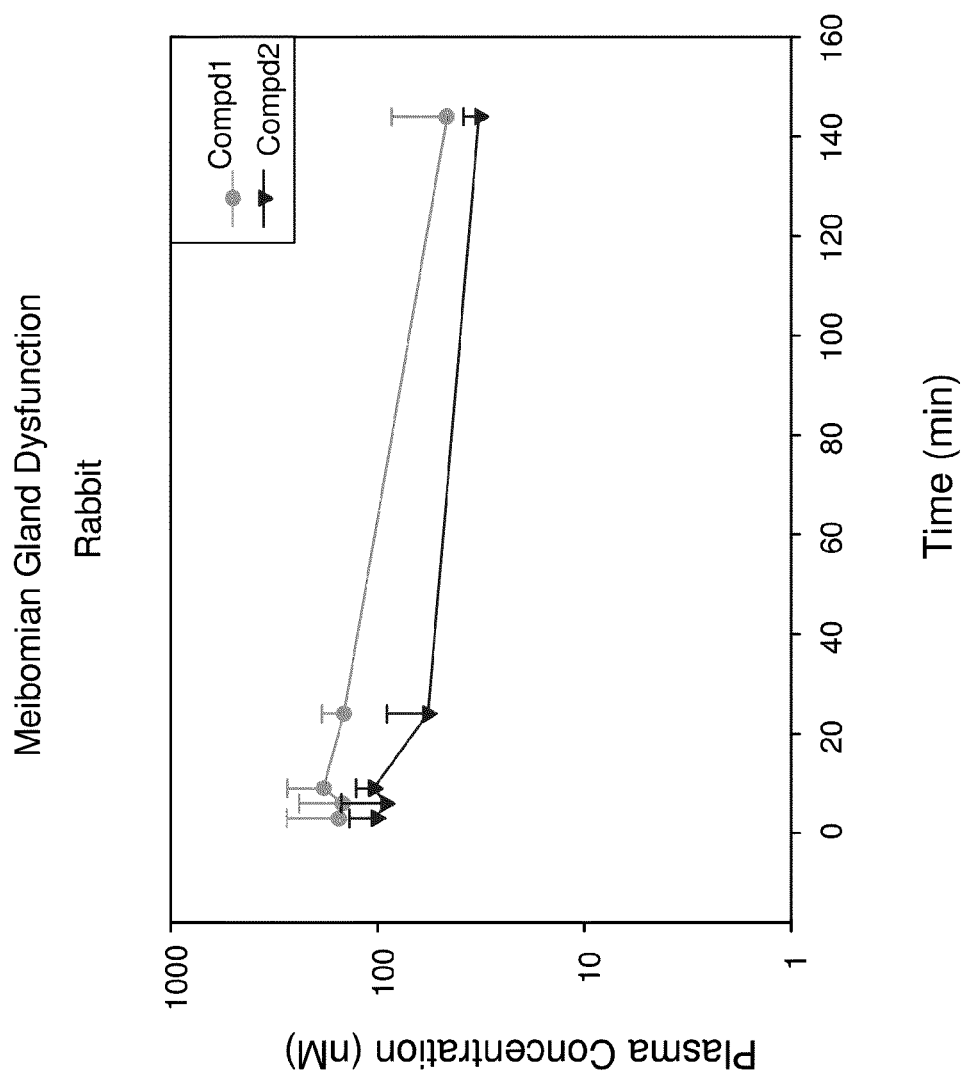
FIG. 4 depicts the pharmacokinetic analysis of rabbit plasma samples after 10 days of dosing as described in Example 4.

Systemic exposures after topical administration of the drugs were determined by collecting peripheral blood samples at 30, 60, 90, 240 and 1440 minutes after drug administration. FIG. 4 shows the pharmacokinetic analysis of rabbit plasma samples after 10 days of dosing. The mean plasma concentrations over time (AUC) Compound 1 and Compound 2 were 25.2 (±9.57) µM/hr and 12.2 (±4.93) µM/hr, respectively, indicating significant differences in systemic absorption of the drugs following topical administration in the same vehicle.

In this study, the composition of fatty acids from tears, Meibomian glands and harderian glands of rabbits was evaluated. The data indicates that castration decreases the levels of the saturated fatty acid palmitate relative to that of stearate in the tears and Meibomian glands of the rabbits. Treatment with Compound 1 significantly increased the levels of the palmitate (as seen by increased palmitate:stearate ratio) compared to the castrated vehicle treated animals. Compound 2 increased the palmitate:stearate ratios approximately 2.5 times that of the ORX vehicle-treated animals and almost 1.5 fold over that of intact vehicle treated animals. Surprisingly, the large increase in the tear lipid ratios was not accompanied by a concomitant increase in the lipid content of the Meibomian glands in Compound 2-treated animals. However, an increase in lipid content of the harderian glands compared to control animals was seen in these animals, although the variation between individual animals was quite large. Further, the lipid content in the harderian gland was not significantly affected by castration within the two week period examined in this study. The large variations seen in the lipid composition of the glands could be an assay artifact as only a portion of the harderian or Meibomian glands was extracted for lipid analysis. Results from this study show that Compound 2 robustly supports proper Meibomian gland function. Vehicle treatment also caused a modest but lesser increase in palmitate:stearate ratio, indicating a placebo effect.

Example 5

The goal of this study was to determine the effect of dosage amounts of Compounds 1 and 2 on tear composition.

Materials and Methods

Thirty New Zealand white rabbits weighing approximately 3 lbs were allowed to acclimate for two weeks before the start of the study Animals were weighed on day 0 of the study, randomized according to body weight and allotted to the following orchiectomized (ORX) dose groups:

1) ORX, Sham treatment (n=5)
2) ORX, Topical vehicle (n=5)
3) ORX, Topical Compound 1, 1.25 mg/kg (n=5)
4) ORX, Topical Compound 1, 0.625 mg/kg (n=5)
5) ORX, Topical Compound 2, 1.25 mg/kg (n=5)
6) ORX, Topical Compound 2, 0.625 mg/kg (n=5)

Surgery

Surgeries for the study were staggered to limit the maximum number of surgeries per day to six. One animal from each group was entered into the study every day and castration was performed as described below. Animals were pre-medicated with glycopyrrolate (0.02 mg/kg) and anesthesia was induced with a combination of ketamine (15 mg/kg):medetomidine (0.25 mg/kg). Anesthesia was maintained with isoflurane (1 liter/hr). Orchiectomy was performed using a scrotal incision. Animals were reversed from anesthesia using atipamezole (1 mg/kg) SQ. Analgesia was provided with buprenorphine (0.05 mg/kg) SQ immediately after the animal's regained sternal recumbency.

Dosing

Immediately after recovery from anesthesia, the animals were dosed with the appropriate test articles as indicated above. Drug dosing was performed once daily for 14 d. Blood samples were collected on day 11 of dosing at 0, 30, 60, 120, 240 and 1440 minutes post administration and to plasma separated for LCMS analysis of parent drug concentrations. Tears were collected using Schirmer tear strips (Alcon, Tex.) on day 0 before surgery and 24 hours after the last administration of drug (day 15). The tears were stored at −80° C. until shipment for lipid analysis. Lipids were hydrolyzed, extracted from the Schirmer strips, derivatized, and subjected to GC-FID to evaluate the lipid composition. The samples were evaluated for the presence of 28 saturated and unsaturated fatty acids that included methyl caprate (C10:0), methyl laurate (C12:0), methyl 11-dodecenoate (C12:1), methyl myri state (C14:0), methyl myristoleate (C14:1), methyl palmitate (C16:0), methyl palmitoleate (C16:1), methyl stearate (C18:0), methyl oleate (C18:1), methyl vaccenate (C18:1), methyl linoleate (C18:2), methyl gamma linoleate (C18:3), methyl linoleate (C18:3), methyl arachidate (C20:0), methyl 11-eicosenoate (C20:1), methyl 11,14 eicosadinoate (C20:2), methyl 8,11,14 eicosatrienoate (C20:3), methyl eicosapentaenoate (C20:5), methyl behenate (C22:0), methyl erucate (C22:1), methyl 13,16 docosaenoate (C22:2), methyl docosatetraenoate (C22:4), methyl docosapentaenoate (C22:5), methyl docosahexaenoate (C22:6), methyl lignocerate and (C24:0), methyl nervonate (C24:1). Area under the curve for each individual peak was determined using the GC ChemStation software. To normalize for the tear content, the lipid composition was expressed as a ratio of the lipid that was most affected by castration (palmitate) to one which remained relatively constant (stearate).

At the end of the study, the animals were euthanatized. The harderian and Meibomian glands were collected for lipid analysis and snap frozen using an ethanol: dry ice bath. Samples were stored at −80 C until ready to ship for analysis.

Pharmacokinetic Data Analysis

Plasma samples collected after dosing were analyzed using an LCMS/MS method. Briefly, plasma samples were prepared by protein precipitation extraction. (S)—N-(4-Cyano-3-(trifluoromethyl)phenyl)-3-(4-chlorophenoxy)-2-hydroxy-2-methylpropanamide was used as internal standard. The analysis of Compound 1 and Compound 2 was performed using an LC-MS/MS system consisting of an Agilent 1100 HPLC with an MDS/Sciex 4000 Q-Trap™ mass spectrometer. The separation was achieved using a $C_{18}$ analytical column (Alltima™, 2.1×100 mm, 3 µm) protected by a $C_{18}$ guard column (SecurityGuard™ 4.0×2.0 mm ID, Phenomenex). Mobile phase consisted of 60% acetonitrile, 40% water and 0.1% formic acid. Mobile phase was delivered at a flow rate of 0.3 mL/min Multiple reaction monitoring (MRM) scans were performed using curtain gas and a source temperature of 500° C. Molecular ions were formed using an ion spray voltage of −4500 V. Product ions were formed in nitrogen gas at a declustering potential of −55 V (Compound 1), −64 V (Compound 2), and −78 V (Internal standard) and collision energy of −24.0 V (Compound 1, m/z 388.0→117.9), −26.0 V (Compound 2, m/z 406.1→135.9), and −22.4 V (Internal standard, m/z 396.9→241.0). The plasma concentration—time data were analyzed by non-compartmental methods using WinNonlin (Version 3.1, Pharsight Corporation, Mountain View, Calif., USA). The area under the plasma concentration—time curve from time zero to infinity (AUC) was calculated by the trapezoidal rule with extrapolation to time infinity. Table 4 shows the statistical analysis for the tear fatty acid composition.

TABLE 4

| Gonadal Status | Compound | Dose | | Palmitate:Stearate Ratio in Tears |
|---|---|---|---|---|
| Intact | Pre-dose | 0 | Mean | 1.57 |
| | | | S.D. | 0.365 |
| ORX | None | 0 | Mean | 1.41 |
| | | | S.D. | 0.152 |
| ORX | Vehicle | 0 | Mean | 1.78 |
| | | | S.D. | 0.218 |
| ORX | Compound 1 | 1.25 mg/kg | Mean | $2.64^{a,b}$ |
| | | | S.D. | 0.858 |
| ORX | Compound 1 | 0.625 mg/kg | Mean | $2.73^{a,b}$ |
| | | | S.D. | 0.892 |
| ORX | Compound 2 | 1.25 mg/kg | Mean | $3.93^{a,b}$ |
| | | | S.D. | 1.1 |
| ORX | Compound 2 | 0.625 mg/kg | Mean | $2.67^{a,b}$ |
| | | | S.D. | 0.95 |

$^{a}$P < 0.05 as compared to pre-dose intact levels
$^{b}$P < 0.05 as compared to ORX vehicle treated controls.

As can be seen from Table 4, analysis of the pre-dose tear samples showed that the palmitate:stearate ratio was 1.57±0.365. ORX (group 2) animals that did not receive any treatment (sham) showed a marginal decrease (1.41±0.152) in their palmitate:stearate ratio. When the ORX animals were treated with vehicle alone, there was a mild increase in the lipid ratio to 1.78±0.218. In the ORX animals treated with Compound 2, there was a dose dependent increase in the palmitate:stearate ratio (Table 4). Compound 1 also showed an increase of 2.64±0.858 and 2.73±0.892 in the palmitate: stearate ratio on treatment with 0.625 and 1.25 mg/kg of drug, respectively (Table 4). However, no significant dose dependent changes in the palmitate:stearate ratio was seen to in Compound 1 treated animals The increase in palmitate:stearate ratio for Compound 2 was higher than that observed for Compound 1.

Effect of Increasing Doses of Compound 1 and Compound 2 on Lipid Composition in Harderian and Meibomian glands Lipids in rabbit tears are derived from secretions of the harderian and Meibomian glands. Lipid content in the glands was assayed using GCMS. Table 5 shows that harderian glands were most affected by treatment with SARMs. A dose dependent increase in palmitate:strearate ratio was seen with both Compound 1 and Compound 2. The lipid ratio was increased by more than 2-fold by Compound 1 (1.25 mg/kg), while the effect of Compound 2 was even greater with an almost 3-fold increase in the lipid ratio seen at the highest dose tested (1.25 mg/kg). No statistically significant change was seen in the Meibomian gland lipids with either Compound 1 or Compound 2.

TABLE 5

| Gonadal Status | Compound | Dose | | Palmitate:stearate ratio in harderian gland | Palmitate:stearate ratio in Meibomian gland |
|---|---|---|---|---|---|
| ORX | None | 0 | Mean | 2.05 | 3.52 |
| | | | S.D. | 0.408 | 0.597 |
| ORX | Vehicle | 0 | Mean | 1.86 | 3.53 |
| | | | S.D. | 0.356 | 0.942 |
| ORX | Compound 1 | 0.625 mg/kg | Mean | $3.45^{a,b}$ | 3.29 |
| | | | S.D. | 0.598 | 1.01 |
| ORX | Compound 1 | 1.25 mg/kg | Mean | $4.87^{a,b}$ | 3.68 |
| | | | S.D. | 1.79 | 1.13 |
| ORX | Compound 2 | 1.25 mg/kg | Mean | $5.30^{a,b}$ | 3.31 |
| | | | S.D. | 1.09 | 0.57 |
| ORX | Compound 2 | 0.625 mg/kg | Mean | $6.09^{a,b}$ | 3.36 |
| | | | S.D. | 2.55 | 0.548 |

$^{a}$P < 0.05 as compared to ORX sham controls
$^{b}$P < 0.05 as compared to ORX vehicle treated controls Pharmacokinetic Analysis of Rabbit Plasma:

Systemic exposures after topical administration of the blood was determined in peripheral blood samples obtained at 30, 60, 90, 240 and 1440 minutes after drug administration on day 11 of the study. As can be seen from Table 6, the systemic exposures (i.e., AUC values) of Compound 2 increased from 3.2 µM*hr to 6.92 µM*hr with increasing dose from 0.625 to 1.25 mg/kg. Compound 1 exposures showed a increase in levels from 2.87 µM*hr to 3.99 µM*hr with increasing dose from 0.625 to 1.25 mg/kg.

TABLE 6

| Drug | Systemic AUC (µM * hr) |
|---|---|
| Compound 1, 0.625 mpk | 2.87 |
| Compound 1, 1.25 mpk | 3.99 |
| Compound 1, 2.5 mpk | 25.2 |
| Compound 2, 0.625 mpk | 3.20 |
| Compound 2, 1.25 mpk | 6.92 |
| Compound 1, 2.5 mpk | 12.2 |

In this study, the composition of fatty acids from tears, Meibomian glands and harderian glands of rabbits after treatment with Compounds 1 and 2 was evaluated. The data indicates that ORX decreased the levels of the saturated fatty acid palmitate in the tears and harderian glands of the rabbits. Palmitate is a saturated fatty acid and is the normal product of the fatty acid synthesis pathway. Palmitate is the precursor for formation of long chain saturated and unsaturated fatty acids. Any reduction in the precursor molecule will progressively lead to a deficiency in the levels of the other fatty acids. Reduction in fatty acids can then lead to instability in tear film formation, leading to a variety of disorders encompassed by Meibomian gland disease. Similar to the results given above, treatment with Compound 1 and Compound 2 increased the palmitate:stearate ratio of the tears compared to that of ORX animals. By using lower doses, the amount of drug absorbed into the systemic circulation was reduced by $\frac{1}{8}^{th}$ and $\frac{1}{4}^{th}$ for Compound 1 and Compound 2, respectively, when compared to the exposure at the 2.5 mg/kg dose (Table 6). This reduction in systemic exposure occurred without losing efficacy in altering lipid composition of the tears. Further the dose of Compound 1 and Compound 2 used was sufficient to stimulate lipid production in the harderian gland 2-3 fold compared to the placebo vehicle treated animals. These data show that systemic exposure is not required for altering function in the local tissues and that a method of ocular delivery through the eyelid is sufficient for preventing hormone deficiency induced lipid alterations in tear composition.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating a Meibomian gland dysfunction in the margins of an eye of a subject, comprising administering to the subject in need thereof an effective amount of a compound of formula I:

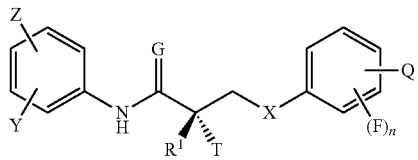

wherein
X is O;
G is O;
Z is $NO_2$ or CN;
Y is $CF_3$;
Q is CN;
T is OH, OR or NHCOR;
R is alkyl, aryl, alkenyl, halogen or OH;
$R^1$ is $CH_3$, $CF_3$, $CH_2F$, $CHF_2$, $CH_2CH_3$ or $CF_2CF_3$ and
n is 0 or 1;
or its isomer, pharmaceutically acceptable salt, pharmaceutical product, N-oxide, hydrate, or any combination thereof;
wherein the treating results in normalization of abnormal Meibomian gland secretions with an improvement in tear lipid composition, an increase in tear fatty acid content and an increase in the palmitate:stearate ratio of the abnormal Meibomian gland secretions in the eye of the subject having Meibomian gland dysfunction.

2. The method of claim 1 wherein said compound is selected from the following structures:

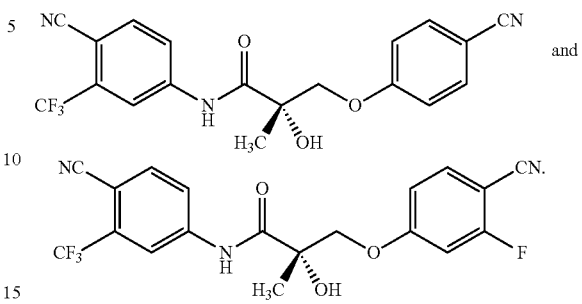

3. The method of claim 1, wherein the number of plugged Meibomian glands is decreased after treatment.
4. The method of claim 1, wherein tear film break up time is increased after treatment.
5. The method of claim 1, wherein Meibomian gland secretion viscosity is decreased after treatment.
6. The method of claim 1, wherein Meibomian gland secretion transparency is increased after treatment.
7. The method of claim 1, wherein the time period between Meibomian gland secretions is reduced after treatment.
8. The method of claim 1, wherein said administering comprises topically applying said pharmaceutical product to the margins of the eye of said subject, wherein said pharmaceutical product is an ophthalmic solution, suspension, elixir, gel, ointment or cream.
9. The method of claim 1, wherein said administering comprises orally administering said pharmaceutical product, wherein said pharmaceutical product is a tablet or a capsule formulation.
10. The method of claim 1, wherein said method comprises reducing the sensation of a foreign body in the eye of the subject.
11. The method of claim 10, wherein said compound is selected from the following structures:

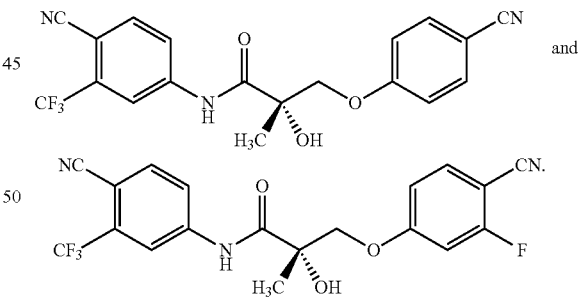

12. The method of claim 10, wherein said administering comprises topically applying said pharmaceutical product to the margins of the eye of said subject, wherein said pharmaceutical product is an ophthalmic solution, suspension, elixir, gel, ointment or cream.
13. The method of claim 10, wherein said administering comprises orally administering said pharmaceutical product, wherein said pharmaceutical product is a tablet or a capsule formulation.
14. The method of claim 1, wherein said Meibomian gland dysfunction comprises redness of the eyelid margin of the subject.

15. The method of claim 14, wherein said compound is selected from the following structures:

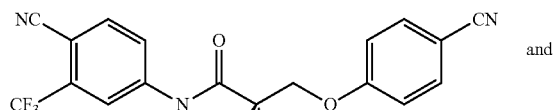
and
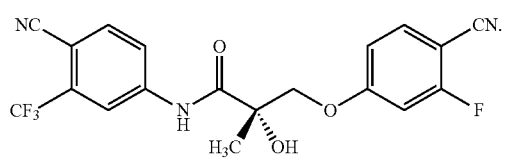

16. The method of claim 14, wherein said redness is reduced and measured photometrically or visually.

17. The method of claim 14, wherein said administering comprises topically applying said pharmaceutical product to the margins of the eye of said subject, wherein said pharmaceutical product is an ophthalmic solution, suspension, elixir, gel, ointment or cream.

18. The method of claim 14, wherein said administering comprises orally administering said pharmaceutical product, wherein said pharmaceutical product is a tablet or a capsule formulation.

19. The method of claim 1 wherein said method comprises improving tear film break up time.

20. The method of claim 19, wherein said compound is selected from the following structures:

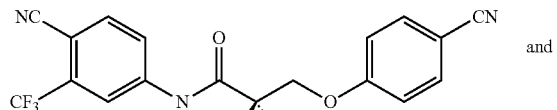
and
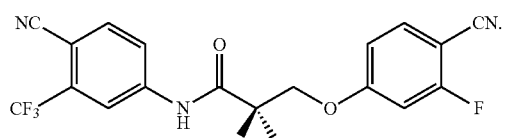

21. The method of claim 19, wherein the tear film break up time is increased after treatment.

22. The method of claim 19, wherein the tear film break up time is decreased after treatment.

23. The method of claim 19, wherein said administering comprises topically applying said pharmaceutical product to the margins of the eye of said subject, wherein said pharmaceutical product is an ophthalmic solution, suspension, elixir, gel, ointment or cream.

24. The method of claim 19, wherein said administering comprises orally administering said pharmaceutical product, wherein said pharmaceutical product is a tablet or a capsule formulation.

25. The method of claim 1, wherein said method comprises improving plugging of Meibomian glands.

26. The method of claim 25, wherein said compound is selected from the following structures:

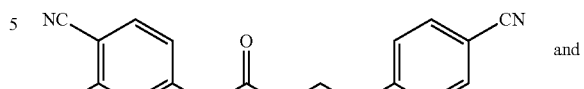
and
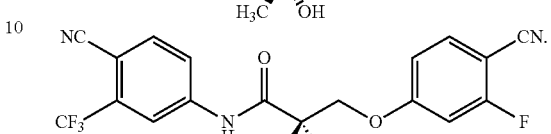

27. The method of claim 25, wherein the plugging of Meibomian glands is decreased after treatment.

28. The method of claim 25, wherein the redness of the eyelid margin is reduced after treatment.

29. The method of claim 25, wherein said administering comprises topically applying said pharmaceutical product to the margins of the eye of said subject, wherein said pharmaceutical product is an ophthalmic solution, suspension, elixir, gel, ointment or cream.

30. The method of claim 23, wherein said administering comprises orally administering said pharmaceutical product, wherein said pharmaceutical product is a tablet or a capsule formulation.

31. The method of claim 1, wherein said method comprises altering the phase transition temperature of lipids in tears.

32. The method of claim 31, wherein said compound is selected from the following structures:

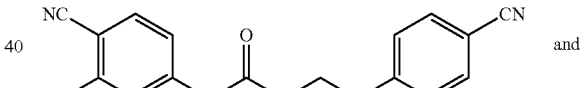
and
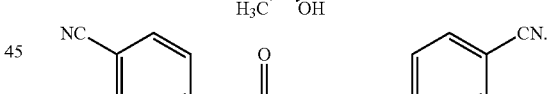

33. The method of claim 31, wherein the phase transition temperature is decreased after treatment.

34. The method of claim 31, wherein said administering comprises topically applying said pharmaceutical product to the margins of the eye of said subject, wherein said pharmaceutical product is an ophthalmic solution, suspension, elixir, gel, ointment or cream.

35. The method of claim 31, wherein said administering comprises orally administering said pharmaceutical product, wherein said pharmaceutical product is a tablet or a capsule formulation.

36. The method of claim 1, wherein said method comprises reducing ocular or conjunctival staining.

37. The method of claim 36, wherein said compound is selected from the following structures:

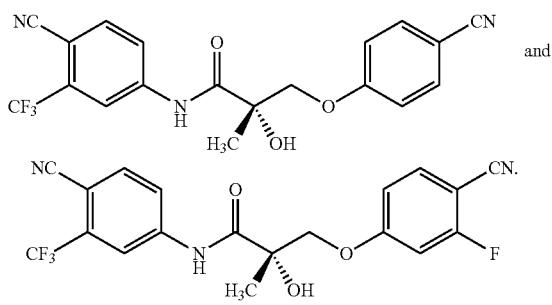

38. The method of claim 36, wherein said administering comprises topically applying said pharmaceutical product to the margins of the eye of said subject, wherein said pharmaceutical product is an ophthalmic solution, suspension, elixir, gel, ointment or cream.

39. The method of claim 36, wherein said administering comprises orally administering said pharmaceutical product, wherein said pharmaceutical product is a tablet or a capsule formulation.

40. The method of claim 1, wherein said method comprises improving burning and/or itching in the eye.

41. The method of claim 40, wherein said compound is selected from the following structures:

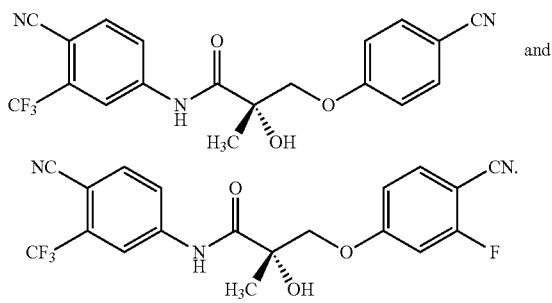

42. The method of claim 40, wherein the burning and/or itching in the eye is reduced after treatment.

43. The method of claim 40, wherein said administering comprises topically applying said pharmaceutical product to the margins of the eye of said subject, wherein said pharmaceutical product is an ophthalmic solution, suspension, elixir, gel, ointment or cream.

44. The method of claim 40, wherein said administering comprises orally administering said pharmaceutical product, wherein said pharmaceutical product is a tablet or a capsule formulation.

45. The method of claim 1, wherein said method comprises reducing the frequency of administration of artificial tears to the eye.

46. The method of claim 45, wherein said compound is selected from the following structures:

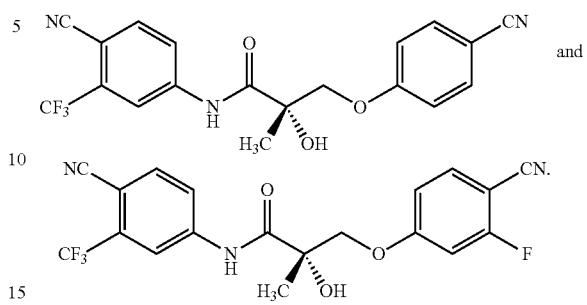

47. The method of claim 45, wherein said administering comprises topically applying said pharmaceutical product to the margins of the eye of said subject, wherein said pharmaceutical product is an ophthalmic solution, suspension, elixir, gel, ointment or cream.

48. The method of claim 45, wherein said administering comprises orally administering said pharmaceutical product, wherein said pharmaceutical product is a tablet or a capsule formulation.

49. The method of claim 1, wherein said method comprises reducing the requirement of steroid therapy to the eye.

50. The method of claim 49, wherein said compound is selected from the following structures:

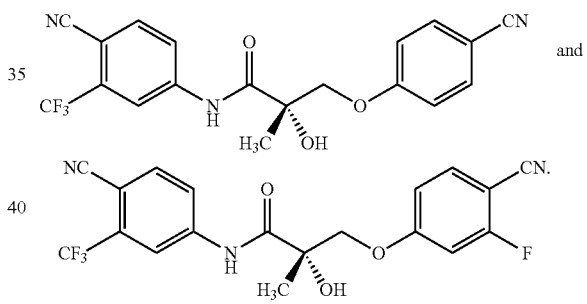

51. The method of claim 49, wherein said administering comprises topically applying said pharmaceutical product to the margins of the eye of said subject, wherein said pharmaceutical product is an ophthalmic solution, suspension, elixir, gel, ointment or cream.

52. The method of claim 49, wherein said administering comprises orally administering said pharmaceutical product, wherein said pharmaceutical product is a tablet or a capsule formulation.

* * * * *